US008680368B2

(12) United States Patent
Saijo et al.

(10) Patent No.: US 8,680,368 B2
(45) Date of Patent: Mar. 25, 2014

(54) METHOD OF EXPRESSION OF FOREIGN GENE IN PLANT INDUCED BY CHEMICAL SUBSTANCE

(75) Inventors: Takanori Saijo, Toyonaka (JP); Akitsu Nagasawa, Kobe (JP)

(73) Assignee: Sumitomo Chemical Company, Limited, Tokyo (JP)

(*) Notice: Subject to any disclaimer, the term of this patent is extended or adjusted under 35 U.S.C. 154(b) by 271 days.

(21) Appl. No.: 12/529,957

(22) PCT Filed: Mar. 7, 2008

(86) PCT No.: PCT/JP2008/054688
§ 371 (c)(1),
(2), (4) Date: Sep. 4, 2009

(87) PCT Pub. No.: WO2008/111661
PCT Pub. Date: Sep. 18, 2008

(65) Prior Publication Data
US 2011/0247095 A1 Oct. 6, 2011

(30) Foreign Application Priority Data

Mar. 8, 2007 (JP) ................. 2007-058307
Jul. 27, 2007 (JP) ................. 2007-195782
Jan. 8, 2008 (JP) ................. 2008-001027

(51) Int. Cl.
*C12N 15/82* (2006.01)
*A01H 5/00* (2006.01)
*C07H 21/04* (2006.01)

(52) U.S. Cl.
USPC ........... 800/288; 800/278; 800/295; 800/298; 536/23.1; 536/23.7; 536/24.1

(58) Field of Classification Search
None
See application file for complete search history.

(56) References Cited

U.S. PATENT DOCUMENTS

| | | | |
|---|---|---|---|
| 5,447,858 A | 9/1995 | Key et al. | |
| 5,489,527 A | 2/1996 | Wilson | |
| 5,847,102 A | 12/1998 | Singh et al. | |
| 5,942,662 A | 8/1999 | Ryals et al. | |
| 6,063,985 A | 5/2000 | Chua et al. | |
| 2002/0164585 A1 | 11/2002 | Chapman et al. | |
| 2004/0214318 A1* | 10/2004 | Chapman et al. | 435/320.1 |
| 2006/0277620 A1 | 12/2006 | Hodges | |
| 2011/0257013 A1 | 10/2011 | Saijo et al. | |

FOREIGN PATENT DOCUMENTS

| | | |
|---|---|---|
| JP | 2003-79372 A | 3/2003 |
| WO | WO 93/21334 A1 | 10/1993 |
| WO | WO 00/39300 * | 7/2000 ............ C12N 15/31 |
| WO | WO-00/39300 A1 | 7/2000 |
| WO | WO-2006/005520 A3 | 1/2006 |

OTHER PUBLICATIONS

Peng et al. Improvement of copper-inducible gene expression system for plant. (2003) Acta Botanica Sinica; vol. 45; pp. 1307-1311.*
Aoyama et al., "A Glucocorticoid-mediated Transcriptional Induction System in Transgenic Plants," The Plant Journal, vol. 11, No. 3, 1997, pp. 605-612.
Benfey et al., "The Cauliflower Mosaic Virus 35S Promoter: Combinatorial Regulation of Transcription in Plants," Science, vol. 250, Nov. 16, 1990, pp. 959-966.
Caddick et al., "An Ethanol Inducible Gene Switch for Plants Used to Manipulate Carbon Metabolism," Nature Biotechnology, vol. 16, Feb. 1998, pp. 177-180.
Chilean Office Action dated Jan. 13, 2012 for Chilean Application No. 0686-2008, with partial English translation.
Gallie et al., "The 5'-leader Sequence of Tobacco Mosaic Virus RNA Enhances the Expression of Foreign Gene Transcripts in Vitro in Vivo," Nucleic Acids Research, vol. 15, No. 8, 1987, pp. 3257-3273.
Gallie et al., "The Ribosomal Fraction Mediates the Translational Enhancement Associated with the 5'-leader of Tobacco Mosaic Virus," vol. 16, No. 17, 1988, pp. 8675-8694.
Japanese Office Action dated Dec. 20, 2011 for Japanese Application No. 2008-001027, with English translation.
Jensen et al., "Mapping of the DNA Binding Domain of the Copper-responsive Transcription Factor Mac1 from *Saccharomyces cerevisiae*," The Journal of Biological Chemistry, vol. 273, No. 37, Issue of Sep. 11, 1998, pp. 23805-23811.
Mett et al., "A System for Tissue-specific Copper-controllable Gene Expression in Transgenic Plants: Nodule-specific Antisense of Asparate Aminotransferase-P2," Transgenic Research, vol. 5, 1996, pp. 105-113.
Mett et al., "Copper-controllable Gene Expression System for Whole Plants," Proceedings of the National Academy of Sciences of the United States of America, vol. 90, May 1993, pp. 4567-4571.
Moore et al., "Transactivated and Chemically Inducible Gene Expression in Plants," The Plant Journal, vol. 45, 2006, pp. 651-683.
Padidam, "Chemically Regulated Gene Expression in Plants," Current Opinion in Plant Biology, vol. 6, 2003, pp. 169-177.
Peña et al., "Dynamic Regulation of Copper Uptake and Detoxification Genes in *Saccharomyces cerevisiae*," Molecular and Cellular Biology, vol. 18, No. 5, May 1998, pp. 2514-2523.

(Continued)

*Primary Examiner* — Cathy Kingdon Worley
(74) *Attorney, Agent, or Firm* — Birch, Stewart, Kolasch & Birch, LLP

(57) ABSTRACT

There is provided an expression method of a target foreign gene in a plant induced by a chemical substance, which comprises a step of activating with copper ions a transcription factor encoded by a foreign gene different from the target foreign gene to induce activation of transcription of the target foreign gene by a region having a promoter function contained in the target foreign gene, wherein a nucleotide sequence encoding said transcription factor is contained in a gene construct which is constructed so as to comprise a nucleotide sequence of a 5'-untranslated region of an arbitrary foreign gene downstream from the region having a promoter function contained in the target foreign gene.

4 Claims, 4 Drawing Sheets

(56) References Cited

OTHER PUBLICATIONS

Weinmann et al., "A Chimeric Transactivator Allows Tetracycline-responsive Gene Expression in Whole Plants" The Plant Journal, vol. 5, No. 4, 1994, pp. 559-569.

English translation of International Preliminary Report on Patentability (Form PCT/IB/373) and of the Written Opinion of the International Searching Authority (Form PCT/ISA/237) issued on Sep. 8, 2009 in PCT/JP2008/054688 (International filing date Mar. 7, 2008).

Peng et al., "Improvement of Copper-inducible Gene Expression System for Plant", Acta Botanica Sinica, 2003, vol. 45, No. 11, pp. 1307-1311.

Craft et al., "New pOp/LhG4 vectors for stringent glucocorticoid-dependent transgene expression in *Arabidopsis*", The Plant Journal, 2005, vol. 41, pp. 899-918, XP-002491436.

Watanabe et al., "Addition of nucleotides similar to deleted CAA repeats in the 5' non-coding region of tomato mosaic virus RNA following propagation", Journal of General Virology, 1996, vol. 77, pp. 2353-2357, XP-002491437.

Satoh et al., "The 5'-Untranslated Region of the Tobacco *Alcohol Dehydrogenase* Gene Functions as an Effective Translational Enhancer in Plant" Journal of Bioscience and Bioengineering, vol. 98, No. 1, pp. 1-8, 2004, XP-002491438.

De Amicis et al., "Improvement of the pBI121 plant expression vector by leader replacement with a sequence combining a poly(CAA) and a CT motif ", Transgenic Res, 2007, vol. 16, pp. 731-738, XP-002491439.

Machine generated English translation of JP-2003-79372-A dated Mar. 18, 2003.

Australian Office Action, dated Jan. 2, 2013, for Australian Application No. 2008225371.

Qin et al., "Effect of UTRs from TMV-RNA on the expression of foreign gene in transgenic plants", Chinese Science Bulletin, vol. 45, No. 18, Sep. 2000, pp. 1681-1685.

Schwechheimer et al., "The activities of acidic and glutamine-rich transcriptional activation domains in plant cells: design of modular transcription factors for high-level expression", Plant Molecular Biology, vol. 36, 1998, pp. 195-204.

Taiwanese Office Action for Taiwanese Application No. 097107996 dated Jun. 26, 2013 (with English translation).

Summons to attend oral proceedings pursuant to Rule 115(1) EPC which issued in European Patent Application No. 08722085.1 on Dec. 13, 2013.

Bohner et al., "Transcriptional activator TGV mediates dexamethasone-inducible and tetracycline-inactivatable gene expression," The Plant Journal, vol. 19, No. 1, 1999, pp. 87-95.

Shiro et al., "Variants of the Cauliflower Mosaic Virus 35S Promoter for Enhanched Gene Expression in Transgenic Tobacco," Res. Bull. Aichi Agric. Res. Ctr., vol. 34, 2002, pp. 55-59. (with English Abstract).

The Office Action (including English translation), dated Feb. 4, 2014, issued in the corresponding Japanese Patent Application No. 2012-133673.

The Office Action, dated Dec. 3, 2013, issued in the corresponding Canadian Patent Application No. 2,679,972.

Zuo et al., "An estrogen receptor-based transactivator XVE mediates highly inducible gene expression in transgenic plants," The Plant Journal, vol. 24, No. 2, 2000, pp. 265-273.

\* cited by examiner

METHOD OF EXPRESSION OF FOREIGN GENE IN PLANT INDUCED BY CHEMICAL SUBSTANCE

TECHNICAL FIELD

The present invention relates to a method of expression of a foreign gene in a plant induced by a chemical substance.

BACKGROUND ART

When a target foreign gene is introduced into and expressed in a plant, a constitutive promoter that is expressed at all times, such as a cauliflower mosaic virus (CaMV) 35S promoter (e.g., Benfey P N & Chua N H, 1990, Science 250, 959-966) is often used. However, in the case of using such a constitutive promoter, a heavy burden is posed on transcription and translation systems, and depending on a kind of a target foreign gene, adverse effects such as inhibition of germination and growth may be sometimes given to a plant. As a method of avoiding such adverse effects, a method of inducing and expressing a target foreign gene at a desired time can be mentioned. By utilizing such an induced expression method, it becomes possible to express a target foreign gene more efficiently, thereby to realize enhanced production of a target foreign protein, etc., encoded by a structural gene region contained in the foreign gene, to control growth and physiology of a plant freely, whose industrial utility value is invaluable.

Methods for induced expression of a target foreign gene at a desired time can be broadly classified into two methods according to the difference in inducing conditions. Namely, there are a method for expression induced by a non-chemical substance such as temperature, light, or a plant pathogen; and a method for expression induced by a chemical substance.

Examples of the former method include a heat inducible system (e.g., U.S. Pat. No. 5,447,858), a low-temperature inducible system (e.g., U.S. Pat. No. 5,847,102) and a system induced by attack of a plant pathogen (e.g., U.S. Pat. No. 5,942,662). These systems utilize only a gene construct having such a very simple structure that an inducible promoter is linked to an upstream region from a target foreign gene. However, in the case of expression induced by a non-chemical substance such as temperature, light, or a plant pathogen, there is a risk that a target foreign gene is abruptly expressed by an unexpected change of an environment, attack of a plant pathogen, or the like.

On the other hand, examples of the latter method include a copper ion-inducible system (e.g., Mett V L et al, 1993, Proc Natl Acad Sci 90, 4567-4571), a steroid hormone-inducible system (e.g., Aoyama T & Chua N H, 1997, Plant J. 11, 605-612; U.S. Pat. No. 6,063,985), an ethanol-inducible system (e.g., Caddick M X et al, 1998, Nature Biotech. 16, 177-180; WO 93/21334) and a tetracycline-inducible system (e.g., Weinmann P et al, 1994, Plant J. 5, 559-569). These have been explained in detail by Moore I et al (Moore I et al, 2006, Plant J 45, 651-683) and Padidam M (Padidam M, 2003, Current Opin Plant Biol 6, 169-177), and the expression of a target foreign gene can be controlled depending on the concentration of a specific chemical substance. Namely, the expression of a target foreign gene can be induced to a necessary amount at a desired time.

Conventionally, in order to produce a target foreign protein that is encoded by a structural gene region contained in a target foreign gene in a recombinant plant (accumulation in the plant), there are some methods which utilize an Ω sequence of a tobacco mosaic virus (TMV) (e.g., Gallie D et al, 1987, Nucleic Acid Res 15, 3257-3273; U.S. Pat. No. 5,489,527) or a 5'-untranslated region sequence of a tobacco alcohol dehydrogenase gene (e.g., Satoh J et al, 2004, J Biosci Bioeng 98(1):1-8; JP 2003-079372 A) to be located upstream from a structural gene region contained in a target foreign gene. On the other hand, there is a report showing that a mRNA linked to an Ω sequence is easily degraded by a nuclease (e.g., Gallie D et al, 1988, Nucleic Acid Res 16, 8675-8694). Then, what kind of results is brought by utilizing a 5'-untranslated region sequence cannot be readily presumed. Besides, it has been totally unknown what kind of influence is brought on expression of a target foreign gene induced by a chemical substance in a specific inducible system (for example, a copper ion-inducible system, etc.)

DISCLOSURE OF THE INVENTION

In an ideal method of expression of a target foreign gene induced by a chemical substance in a plant, a very high expression level of the target foreign gene is desired during induction, while an expression level of the target foreign gene during non-induction should be very low. The lower an expression level of a target gene during non-induction, the smaller the load to a host plant is. In addition, it becomes possible to control a signal factor, etc., which functions in a small amount. Further, the higher the expression level of a target foreign gene during induction, the more efficiently it becomes possible to produce a target foreign protein etc. encoded by the structural gene region contained in the target foreign gene, and the less stimulus necessary for induction is required as well.

Among the expression of a target foreign gene induced by a chemical substance in the above-mentioned inducible systems, regarding a copper ion-inducible system, there is a problem that the system has a low induction ratio of induced expression (e.g., Padidam M, 2003, Current Opin Plant Biol 6, 169-177). An object of the present invention is to provide a system capable of improvement of an induction ratio of induced expression of a target foreign gene in a copper ion-inducible system to realize an ideal method of expression of a target foreign gene in a plant induced by copper ions.

Namely, the present invention provides:

1. A method of expression of a target foreign gene in a plant induced by a chemical substance, which comprises a step of activating with copper ions a transcription factor encoded by a foreign gene different from the target foreign gene to induce activation of transcription of the target foreign gene by a region having a promoter function contained in the target foreign gene, wherein a nucleotide sequence encoding said transcription factor is contained in a gene construct which is constructed so as to comprise a nucleotide sequence of a 5'-untranslated region of an arbitrary foreign gene downstream from the region having a promoter function contained in the target foreign gene (hereinafter, sometimes, referred to as the present induced expression method);

2. The method according to the above item 1, wherein the nucleotide sequence of said 5'-untranslated region is that selected from the group consisting of the following nucleotide sequence group concerning a 5'-untranslated region:

(1) a nucleotide sequence derived from a 5'-untranslated region of a gene of a virus or an inducible gene of a plant;

(2) a nucleotide sequence derived from a 5'-untranslated region of a gene of a virus belonging to *Tobamovirus* genus;

(3) a nucleotide sequence derived from a 5'-untranslated region of a gene of tomato mosaic virus; and (4) a nucleotide sequence derived from a 5'-untranslated region of a 130k/180k gene of tomato mosaic virus;

3. The method according to the above item 1 or 2, wherein the nucleotide sequence encoding said transcription factor is that selected from the group consisting of the following nucleotide sequence group concerning a transcription factor:

(1) a nucleotide sequence derived from a nucleotide sequence encoding a eukaryote transcription factor;

(2) a nucleotide sequence derived from a nucleotide sequence encoding a yeast transcription factor; and (3) a nucleotide sequence derived from a nucleotide sequence encoding the yeast ACE1;

4. The method according to the above item 1, 2 or 3, wherein said gene construct is constructed so as to additionally comprise a nucleotide sequence encoding a transcriptional activation region located downstream from the nucleotide sequence encoding said transcription factor, and wherein the transcriptional activation region is that of a transcription factor different from said transcription factor;

5. The method according to the above item 4, wherein the nucleotide sequence encoding said transcriptional activation region is a nucleotide sequence selected from the group consisting of the following nucleotide sequence group concerning a transcriptional activation region:

(1) a nucleotide sequence derived from a nucleotide sequence encoding a transcriptional activation region of a transcription factor of a virus;

(2) a nucleotide sequence derived from a nucleotide sequence encoding a transcriptional activation region of a transcription factor of a virus belonging to Simplexvirus genus, (3) a nucleotide sequence derived from a nucleotide sequence encoding a transcriptional activation region of a transcription factor of Herpes simplex virus; and (4) a nucleotide sequence derived from a nucleotide sequence encoding a transcriptional activation region of a VP16 transcription factor of Herpes simplex virus;

6. The method according to the above item 1, 2, 3, 4 or 5, wherein said gene construct is constructed so as to additionally comprise an arbitrary promoter upstream from the nucleotide sequence encoding said transcription factor;

7. A gene construct for expression of a target foreign gene in a plant induced by a chemical substance (hereinafter, sometimes, referred to as the gene construct of the present invention), said construct comprising:

(a) a target foreign gene comprising a region having a promoter function and a structural gene region encoding a target foreign protein;

(b) a nucleotide sequence encoding a transcription factor encoded by a foreign gene different from said target foreign gene, wherein said transcription factor can be activated by copper ions; and (c) a nucleotide sequence of a 5'-untranslated region of an arbitrary foreign gene located downstream from the region having a promoter function contained in said target foreign gene (hereinafter, sometimes, referred to as the present promoter region);

8. The gene construct according to the above item 7, wherein the nucleotide sequence of said 5'-untranslated region is that selected from the group consisting of the following nucleotide sequence group concerning a 5'-untranslated region:

(1) a nucleotide sequence derived from a 5'-untranslated region of a gene of a virus or an inducible gene of a plant;

(2) a nucleotide sequence derived from a 5'-untranslated region of a gene of a virus belonging to *Tobamovirus* genus;

(3) a nucleotide sequence derived from a 5'-untranslated region of a gene of tomato mosaic virus; and (4) a nucleotide sequence derived from a 5'-untranslated region of a 130k/180k gene of tomato mosaic virus;

9. The gene construct according to the above item 7 or 8, wherein the nucleotide sequence of said transcription factor is that selected from the group consisting of the following nucleotide sequence group concerning a transcription factor:

(1) a nucleotide sequence derived from a nucleotide sequence encoding a eukaryote transcription factor;

(2) a nucleotide sequence derived from a nucleotide sequence encoding a yeast transcription factor; and (3) a nucleotide sequence derived from a nucleotide sequence encoding a yeast ACE1;

10. The gene construct according to the above item 7, 8 or 9, which is constructed so as to additionally comprise a nucleotide sequence encoding a transcriptional activation region located downstream from the nucleotide sequence encoding said transcription factor, wherein the transcriptional activation region is that of a transcription factor different from said transcription factor;

11. The gene construct of the above item 10, wherein the nucleotide sequence encoding said transcriptional activation region is a nucleotide sequence selected from the group consisting of the following nucleotide sequence group concerning a transcriptional activation region:

(1) a nucleotide sequence derived from a nucleotide sequence encoding a transcriptional activation region of transcription factor of a virus;

(2) a nucleotide sequence derived from a nucleotide sequence encoding a transcriptional activation region of a transcription factor of a virus belonging to Simplexvirus genus;

(3) a nucleotide sequence derived from a nucleotide sequence encoding a transcriptional activation region of a transcription factor of Herpes simplex virus; and (4) a nucleotide sequence derived from a nucleotide sequence encoding a transcriptional activation region of a VP16 transcription factor of Herpes simplex virus;

12. The gene construct according to the above item 7, 8, 9, 10 or 11, which is a gene construct constructed so as to additionally comprise an arbitrary promoter upstream from the nucleotide sequence encoding said transcription factor;

13. A transformed plant, wherein the gene construct according to any one of the above items 7 to 12 is introduced (hereinafter, sometimes, referred to as the present transformed plant); and 14. A method for obtaining a foreign protein, which comprises recovering a target foreign protein from the transformed plant according to the above item 13 (hereinafter, sometimes, the present method for obtaining a foreign protein).

According to the present invention, in a copper ion-inducible system, it is possible to provide a method capable of improving an induction ratio of induced expression of a target foreign gene in a plant.

BEST MODE FOR CARRYING OUT THE INVENTION

Figure 1:
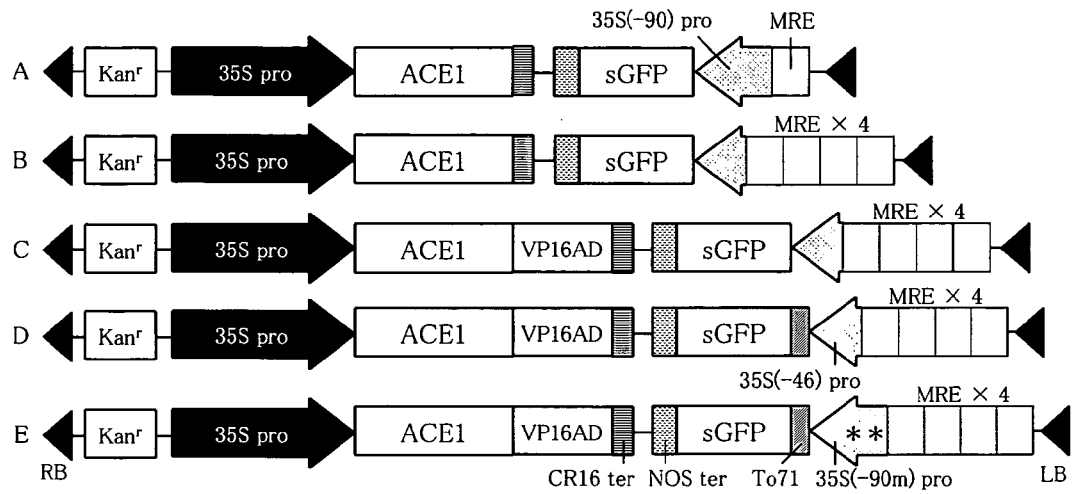
FIG. 1 is a schematic view illustrating the structures of T-DNA regions of copper ion-inducible sGFP gene expression vectors. The symbol "*" in FIG. 1 shows a mutation-introduced region of the as-1 site.

Hereinafter, the present invention will be illustrated in detail.

The gene construct of the present invention can be utilized for expression of a target foreign gene in a plant induced by a chemical substance. The gene construct can comprise:

(a) a target foreign gene comprising a region having a promoter function and a structural gene region encoding a target foreign protein;

(b) a nucleotide sequence encoding a transcription factor encoded by a foreign gene different from said target foreign gene, wherein said transcription factor can be activated by copper ions (hereinafter, sometimes, referred to as the present transcription factor); and (c) a nucleotide sequence of a 5'-untranslated region of an arbitrary foreign gene (hereinafter, sometimes, referred to as the present 5'-untranslated region) located downstream from a region having a promoter function contained in said target foreign gene (hereinafter, sometimes, referred to as the present promoter region).

Examples of the preferred gene construct of the present invention include a gene construct which is constructed so as to additionally comprise a nucleotide sequence encoding a transcriptional activation region downstream from the nucleotide sequence encoding the present transcription factor, wherein the transcriptional activation region (hereinafter, sometimes, referred to as the present transcriptional activation region) is that of a transcription factor different from said transcription factor.

The gene construct of the present invention can comprise each of the above elements (a), (b) and (c). Namely, the gene construct can be constructed so as to have each of the above elements (a), (b) and (c) as one expression cassette. Alternatively, it can be constructed as such two expression cassettes that, for example, one has the above elements (a) and (c), and the other has the above element (b).

Such expression cassettes can be constructed by using a conventional genetic engineering technique. Additionally, in the case where two expression cassettes are constructed, the first expression cassette may have the above elements (a) and (c), and the second expression cassette may have the above element (b).

Preferred examples of the gene construct of the present invention include a gene construct which is constructed so as to additionally comprise an arbitrary promoter upstream from the nucleotide sequence encoding the above-described transcription factor.

Further, as the preferred gene construct of the present invention, there can be mentioned a gene construct that is constructed so as to additionally comprise an arbitrary terminator downstream from the nucleotide sequence encoding the above-described transcription factor. Examples of the terminator include a NOS terminator, CR16 terminator (JP 2000-166577 A), and a soybean seed glycinin terminator (JP 06-189777 A).

The gene construct of the present invention is introduced into, for example, a host plant such as a plant or cultured cells to carry out induced expression of the gene construct. The introduction of the gene construct of the present invention into a host plant can be carried out by a conventional genetic engineering technique according to an appropriate method applicable to a particular host plant.

Specifically, for example, a target foreign gene can be introduced as that contained in a gene construct wherein the first expression cassette and the second expression cassette are linked on a vector. Alternatively, the first expression cassette and the second expression cassette may be introduced without linking into a host plant so as to form the gene construct of the present invention in vivo. For example, these expression cassettes can be introduced by mixing without linking. Further, either a first expression cassette or a second expression cassette can be introduced into a host plant, followed by introduction of the other expression cassette.

Further, crossbreeding can be carried out between an individual into which a first expression cassette has been introduced, and an individual, into which a second expression cassette has been introduced. It is also possible to carry out induced expression of plural kinds of foreign genes by introducing plural kinds of first expression cassettes.

As the method of introducing the gene construct of the present invention, there can be used various known methods such as *Agrobacterium* method, particle gun method, electroporation method, calcium phosphate method, virus vector method, and the like.

Examples of the host plant include species important for agriculture and gardening, or useful in genetics such as genome analysis. Further, the host plant includes arbitrary plant species. Examples thereof include soybean, pea, kidney bean, alfalfa, *Lotus japonicus*, clover, peanut, sweet pea, walnut, tea, cotton, pepper, cucumber, water melon, pumpkin, squash, melon, radish, rapeseed, canola, beet, lettuce, cabbage, broccoli, cauliflower, *Arabidopsis*, tobacco, eggplant, potato, sweet potato, taro, artichoke, tomato, spinach, asparagus, carrot, sesame, endive, chrysanthemum, geranium, antirrhinum, carnation, pink, sweet oleander, Bouvardia, Gypsophilla, gerbera, Russell prairie gentian, tulip, Mathiola incana, Limonium, cyclamen, Saxifraga stolonifera, swamp chrysanthemum, violet, rose, cherry, apple, strawberry, Japanese apricot, orange, Japanese quince, azalea, Barbados nut, gentian, cosmos, morning-glory, sunflower, ginkgo, Japanese cedar, Japanese cypress, poplar, pine, Sequoia, oak, water lily, Eucommia, beech, rice, wheat, barley, rye, oat, corn, maize, green onion, garlic, lily, Tiger lily, orchid, gladiolus and pineapple.

In the induced expression method of the present invention, for example, it is necessary to contact copper ions with the present transformed plant, or to apply copper ions to the present transformed plant. As a contact or application method, in the case where the present transformed plant is culture cells, for example, mixing of copper ions with a culture medium or a nutrient solution (e.g., copper ion concentration: 1 µM to 24 mM) can be mentioned. Further, in the case where the present transformed plant is a plant per se, for example, soil or a stem or leaf of the plant is treated with copper ions, or copper ions are sprayed on a stem or leaf of the plant (e.g., the amount of copper ion: 1 nmol to 2.4 mmol, copper ion concentration: 1 µM to 24 mM). Preferably, an appropriate method is selected according to a particular kind of a host plant and a particular situation. In the induced expression method of the present invention, it is required to penetrate copper ions into plant cells wherein induced expression of a target foreign gene is expected. For the purpose of this penetration, for example, a preparation of a complex of copper ions to be applied can be used. Alternatively, a copper agent for agriculture applications such as Bordeaux (Sumitomo Chemical Co., Ltd.), G-fine (Yashima Chemical Industry Co., Ltd.), Tomono Z-Bordeaux (Tomono Agrica Co., Ltd.), Ridomilpulus (Nihon Nohyaku Co., Ltd.), Highcopper (Sumitomo Chemical Co., Ltd.), CUPRAVIT forte (Bayer CropScience Corporation), Kocide Bordeaux (DuPont Corporation), Kinondo (Agro Kanesho Co., Ltd.) or Yonepon (Yonezawa Chemical Co., Ltd.); or a copper agent to be used as food additives such as copper gluconate (Wako Pure Chemical Industries, Ltd.) can be employed by adjusting to a desired concentration. Further, a spreading agent can be mixed when a preparation or an agent is applied.

The present transcription factor to be used is activated by copper ions to induce transcriptional activity of a region having a promoter function contained in a target foreign gene (i.e., the present promoter region).

The transcription factor is that of an inactive type in the absence of copper ions, and it cannot induce transcriptional activity of a region having a promoter function (i.e., the present promoter region), while in the presence of copper ions, it is changed to that of an active type, which can induce transcriptional activity of a region having a promoter function (i.e., the present promoter region). Usually, a transcription factor has a DNA binding region and a transcriptional activation region. At this time, it is possible to link a transcriptional activation region of a transcription factor different from the present transcription factor to the present transcription factor, or to replace the transcriptional activation region of the original transcription factor with a transcriptional activation region of a transcription factor different from the transcription factor. Additionally, within the cells of a host plant, the present transcriptional activation region has a function to recruit a mediator of a RNA polymerase complex and enhances a transcriptional activation capability.

Examples of a preferable nucleotide sequence of the present transcription factor, as described above, include that selected from the group consisting of the following nucleotide sequence group concerning the transcription factor:

(1) a nucleotide sequence derived from a nucleotide sequence encoding a eukaryote transcription factor, (2) a nucleotide sequence derived from a nucleotide sequence encoding a yeast transcription factor, and (3) a nucleotide sequence derived from a nucleotide sequence encoding a yeast ACE1.

Further, examples thereof include a nucleotide sequence derived from AMT1 of *Candida glabrata* (Thorvaldsen J L et al, 1993, J Biol Chem 268, 12512-12518), a nucleotide sequence derived from CRF1 of *Yarrowia lipolytica* (Garcia S, 2002, J Biol Chem 277, 37359-37369), a nucleotide sequence derived from a transcription factor which causes induced expression of SOD gene groups of corn copper ion-dependently (Ruzza S M et al, 2003, Biochemistry 42, 1508-1516), and the like.

These derived nucleotide sequences include partial sequences thereof, chimeric sequences thereof with other nucleotide sequences, and mutated sequences wherein mutation such as deletion, insertion, replacement, etc. are introduced.

The present promoter region to be used comprises a nucleotide sequence capable of inducing transcriptional activity of the above-described present transcription factor in the present of copper ions. Any region can be used as the present promoter region as far as a target foreign gene can be expressed in the host cells under inducible conditions. Preferably, for example, there can be mentioned one containing MRE sequences of yeast (Mett V L et al, 1993, Proc Natl Acad Sci 90, 4567-4571), or the like. Specifically, there is mentioned one that MRE sequences of yeast etc. are repeatedly located upstream from a TATA sequence present in a region having a promoter function conventionally used.

The above-described region having a promoter function conventionally used may be a constitutive promoter, a tissue-specific promoter, or an inducible promoter that transcriptional activity is induced by a certain stimulus. It is desirable to appropriately select the promoter according to a particular use.

Examples of the constitutive promoter include a CaMV 35S promoter, a PG10-90 (JP 09-131187 A), an ubiquitin promoter (WO 01/094394), an actin promoter (WO 00/070067), and the like. Further, examples of the tissue-specific promoter include a soybean seed glycinin promoter (JP 06-189777 A), a prolamin promoter (WO 2004/056993), a kidney bean seed phaseolin promoter (WO 91/013993), a rapeseed napin promoter (WO 91/013972), *Arabidopsis* Sultr2; 2 promoter (Takahashi H et al, 2000, Plant J 23, 171-182), *Agrobacterium* rolC promoter (Almon E et al, 1997, Physiol 115, 1599-1607), and the like.

The 5'-untranslated region to be used is located downstream from the present promoter, and comprises a nucleotide sequence that is transcribed but not translated. However, in the case where, for example, a target foreign gene encodes an antisense RNA or it encodes an RNA inducing RNAi, the 5'-untranslated region is defined as that from a transcription initiation point to just before a region encoding the RNA. The 5'-untranslated region sequence can be derived from a gene of a virus or an inducible gene of a plant. Examples of the 5'-untranslated region sequence derived from a virus include Ω sequence of tobacco mosaic virus (TMV) (e.g., Gallie D et al, 1987, Nucleic Acid Res 15, 3257-3273; U.S. Pat. No. 5,489,527), L sequence of tobacco etch virus (TEV) (e.g., Linbo J A, 2007, BMC Biotechnol 7, 52), Φ sequence of RSV (e.g., Mori M et al, 2006, Plant Biotechnology 23(1), 55-61), and the like. The inducible gene of a plant means a gene whose expression level is increased by a certain stimulus, and examples thereof include an alcohol dehydrogenase gene of tobacco (Satoh J et al, 2004, J Biosci Bioeng 98(1):1-8; JP 2003-79372 A), PR1a gene of tobacco (Ohshima M et al, 1990, Plant Cell 2(2), 95-106), In2-1 gene of In2-2 gene of corn (WO 90/11361; De Veylder L et al, 1997, Plant Cell Physiol 38(5). 568-577), GST27 gene of corn (Jepson I et al, 1994, Plant Mol Biol 26(6), 1855-1856; WO 97/11189), RD29 gene of *Arabidopsis* (Yamaguchi-Shinozaki K, 1993, Mol Gen Genet. 236(2-3), 331-340), heat shock protein gene of *Arabidopsis*, soybean or sun flower (Yoshida K et al, 1995, Appl Microbiol Biotechnol 44(3-4):466-472; Nagao R T et al, 1985, Mol Cell Biol 5(12), 3417-3428; Almoguera C et al, 2002, J Biol Chem, 277(46):43866-43872), and the like.

Examples of the preferred nucleotide sequence of the present 5'-untranslated region include the following nucleotide sequence group concerning a 5'-untranslated region:

(1) a nucleotide sequence derived from a 5'-untranslated region of a gene of a virus or an inducible gene of a plant;

(2) a nucleotide sequence derived from a 5'-untranslated region of a gene of a virus belonging to Tobamovirus genus (e.g., Gallie D et al, 1987, Nucleic Acid Res 15, 3257-3273; U.S. Pat. No. 5,489,527);

(3) a nucleotide sequence derived from a 5'-untranslated region of a gene of tomato mosaic virus; and (4) a nucleotide sequence derived from a 5'-untranslated region of a 130k/180k gene of tomato mosaic virus.

These derived nucleotide sequences include partial sequences thereof, chimeric sequences thereof with other nucleotide sequences, and mutated sequences wherein mutation such as deletion, insertion, replacement, etc. are introduced.

Further, in the case that the 5'-untranslated region is a sequence having 48 bp or more, or a secondary structure is predicted under conditions of 25° C. with a secondary structure-predicting program: provided by The Bioinformatics Center at Rensselaer and Wadsworth, e.g., see Zuker M, 2003, Nucleic Acids Res 31(13), 3406-3415), there can also be mentioned a nucleotide sequence which has a longest base succession of 11 bp or more whose interaction in the molecule cannot be predicted.

As described above, examples of a preferred nucleotide sequence encoding the present transcriptional activation region include the following nucleotide sequence group concerning a transcriptional activation region:

(1) a nucleotide sequence derived from a nucleotide sequence encoding a transcriptional activation region of a transcription factor of a virus;

(2) a nucleotide sequence derived from a nucleotide sequence encoding a transcriptional activation region of a transcription factor of a virus belonging to Simplexvirus genus, (3) a nucleotide sequence derived from a nucleotide sequence encoding a transcriptional activation region of a transcription factor of Herpes simplex virus; and (4) a nucleotide sequence derived from a nucleotide sequence encoding a transcriptional activation region of a VP16 transcription factor of Herpes simplex virus (e.g., Triezenberg S J et al, 1988, Genes Dev 2(6), 718-729).

Further, examples thereof also include a GAL4 transcription factor (Gill G, Ptashne M, 1987, Cell 51(1), 121-126), peptide AH artificially synthesized having a transcriptional activation capability (Ansari A Z et a, 2001, Chem Biol 8(6), 583-592) and the like.

These derived nucleotide sequences include partial sequences thereof, chimeric sequences thereof with other nucleotide sequences, and mutated sequences wherein mutation such as deletion, insertion, replacement, etc. are introduced.

The transcription factor to be used in the induced expression method of the present invention is the present transcription factor as described above, and a transcription factor encoded by a foreign gene different from a target foreign gene. The transcription factor is activated by copper ions. Further, the gene construct to be used in the induced expression method of the present invention is, for example, the gene construct of the present invention as described above. Furthermore, the 5'-untranslated region of a foreign gene used in the induced expression method of the present invention is the 5'-untranslated region as described above, and the 5'-untranslated region of an arbitrary foreign gene. Moreover, the region having a promoter function to be used in the induced expression method of the present invention is the present promoter region as described above, and the region having promoter function contained in the target foreign gene.

As mentioned above, in the transformed plant of the present invention, the gene construct of the present invention is introduced. In the method of obtaining a foreign protein in the present invention, a target foreign protein can be recovered from the transformed plant according to a conventional protein engineering technique.

Examples of the applications of the present invention will be illustrated below, but the applications are not particularly limited thereto.

*Arabidopsis* in which a FT gene is excessively expressed has an early flowering time (e.g., JP 2000-139250 A). In the case where a target foreign gene in the induced expression of the present invention is a FT gene, it is possible to induce flowering at a desired time. It becomes possible to more strictly control flowering in such a manner that the present FT gene is induced and expressed in a plant whose flowering is made difficult by mutation introduction to a flowering-accelerating gene or induction RNAi of a flowering-accelerating gene; excessive expression of a flowering-decelerating gene.

Incidentally, FT gene is abbreviation of a Flowering Locus T gene, and means a gene encoding a factor that positively functions in regard to flowering control. FT gene has a function that expression is increased at a sieve part of fibrovascular bundle in response to length of day, moves to a top of a stem, and interacts with a bZIP type transcription factor called FD expressed on a top of the stem, thereby to induce flowering (e.g., Kobayashi Y and Weigel D, 2007, Genes Dev 21, 2371-2384).

Tobacco in which collagen genes are introduced produces collagen (e.g., U.S. Pat. No. 6,617,431). In the case where target foreign genes in the induced expression of the present invention are collagen genes, a high-level production becomes possible.

Corn in which a PPO gene is introduced becomes resistant to herbicides (e.g., U.S. Pat. No. 6,307,129). In the case where a target foreign gene in the induced expression method of the present invention is a PPO gene, it becomes resistant to herbicides only at a desired time. When plant cultivation becomes unnecessary, it can be killed with the same herbicides.

Soybean in which an EPSPS gene is introduced becomes resistant to herbicides (e.g., WO 92/00377). In the case where a target foreign gene in the induced expression method of the present invention is an EPSPS gene, it becomes resistant to herbicides only at a desired time. When plant cultivation becomes unnecessary, it can be killed with the same herbicides.

Soybean in which a Δ15 fatty acid-unsaturated enzyme gene is introduced raises the content of highly unsaturated fatty acids (e.g., WO 2005/047479). In the case where a target foreign gene in the inducible expression method of the present invention is a Δ15 fatty acid-unsaturated enzyme gene, it becomes possible to control a fatty acid composition in fats and oils at a desired time.

Rice in which a polyprenyl diphosphate-synthesis gene is introduced raises CoQ10 content (e.g., JP 2006-212019 A). In the case where a target foreign gene in the inducible expression method of the present invention is a polyprenyl diphosphate-synthesis gene, it becomes possible to raise the CoQ10 content at a desired time.

Coffee in which expression of a theobromine synthesis gene is suppressed decreases the content of caffeine (e.g., JP 2002-112785 A; Ogita S et al, 2004, Plant Mol Biol 54(6), 931-941). In the case where a target foreign gene in the induced expression method of the present invention is an antisense gene of a theobromine synthesis gene, it becomes possible to control the content of caffeine in seeds at a desired time.

Crucifer in which a ribonuclease gene is expressed at anther becomes male sterile (e.g., Mariani C et al, 1990, Nature 347, 737-741). In the case where a target foreign gene in the induced expression method of the present invention is a ribonuclease gene, it becomes possible to convert only desired individuals into male sterile. On the other hand, when the expression of an S glycoprotein gene is suppressed, self-incompatibility is broken (e.g., JP 08-322412 A). In the case where a target foreign gene in the induced expression method of the present invention is an antisense gene of an S sugar protein gene, it becomes possible to convert only desired individuals into self-incompatibility. Thus, hybrid seeds can be efficiently collected.

Further, regarding a steroid hormone inducible system, there is the following report (e.g., Zuo J et al, 2006, Methods Mol Biol 323, 329-342).

(1) By induced expression of a CRE DNA recombinase gene, an expression cassette of a drug-resistant gene etc. sandwiched by two loxP sites is cut out.
(2) By induced expression of an RNA triggering RNAi, expression of a desired gene is suppressed.
(3) By induced expression of an mRNA including a donor site and acceptor site of an intron, a desired cDNA is isolated or a cDNA is isolated in a random manner.
(4) By induced expression of a gene on a chromosome that is incorporated accidentally downstream from a 5'-untranslated region without arranging a gene or terminator downstream from a 5'-untranslated region of the first expression cassette, a functional gene is isolated.

As described above, by producing a similar construction, the induced expression method of the present invention can be applied to all of these techniques.

Further, there are some reports showing that a brome mosaic virus cDNA or tomato mosaic virus cDNA in which a region encoding a coat protein is replaced by a structural gene region of a target foreign protein is induced is expressed by steroid hormone to produce a foreign protein at a high level (e.g., JP 2005-102652 A; Mori M et al, 2001, Plant Journal 27(1), 79-86; Dohi K et al, 2006, Arch Virol 151, 1075-1084). In the case where a target foreign gene in the induced expression method of the present invention is a virus cDNA whose structural coding region of a coat protein etc. is replaced with other gene, the replaced structural gene can be induced at a high transcriptional level.

Hereinafter, the present invention will be illustrated in detail with reference to Examples.

Example 1

Preparation of Introduction Vectors (1) Construction of Transcription Factor Gene Expression Cassettes A genome DNA was extracted from budding yeast (*Saccharomyces cerevisiae* strain AH22) cultured with shaking at 30° C. in a YPD medium (1% yeast extract, 2% polypeptone, 2% glucose) for 2 days by using a genome DNA extraction kit "Gen-torukun" (Takara Bio, Inc.). By using the extracted genome DNA as a template, an ACEI transcription factor gene was amplified by PCR using two kinds of specific primers (ACE1-1F, ACE1-1RC). The amplified ACEI transcription factor gene was replaced by a GUS gene of pB1221 (Clontech) to prepare p35S-ACE1-NOS. Next, a NOS terminator contained in the p35S-ACE1-NOS was replaced by a CR16 terminator (JP 2000-166577 A) to prepare p35S-ACE1-CR.

The recombinant *Arabidopsis* seed (No. N70016) purchased from NASC (Nottingham *Arabidopsis* Stock Centre) was sowed on a modified MS agar medium (MS inorganic salts, B5 vitamin, 2% sucrose, 0.8% agar). From the true leaves of the recombinant *Arabidopsis* grown at 23° C. for 3 weeks, genome DNA was extracted using a plant genome DNA extraction kit "DNeasy Plant kit" (QIAGEN).

By using the extracted genome DNA as a template, the transcriptional activation domain (VP16AD) gene of VP16AD transcription factor of Herpes simplex virus was amplified by PCR using two kinds of specific primers (VP16-1F, VP16-1RC). The amplified VP16AD gene was TA-cloned into pCR2.1 (Invitrogen) to prepare pCR2.1-VP16AD. By using the pCR2.1-VP16AD as a template, PCR was carried out using two kinds of specific primers (VP16-2F, VP16-2RC) and mutation was introduced into SacI site in the VP16AD gene to prepare pCR2.1-VP16AD (dSacI). Then, by using the pCR2.1-VP16AD (dSacI) as a template, PCR was carried out using two kinds of specific primers (VP16-3F, VP16-3RC) to add an XhoI site to the 5'-terminal, and SacI site to the 3'-terminal of the VP16AD (dSacI) gene.

By using p35S-ACE1-CR as a template, PCR was carried out using two kinds of specific primers (ACE1-1F, ACE1-1RC) to remove the termination codon of the ACE1 transcription factor gene and to add XhoI site thereto. VP16AD(dSacI) gene was linked to downstream from the ACE1 transcription factor gene to whose 3'-terminal XhoI site has been added so as to fit the reading frame to prepare p35S-ACE1/VP16AD-CR.

```
ACE1-1F:
                                        (SEQ ID NO: 1)
5'-atggatccatggtcgtaattaacggg-3'

ACE1-1RC:
                                        (SEQ ID NO: 2)
5'-tggagctcttattgtgaatgtgagttatg-3'

ACE1-2RC:
                                        (SEQ ID NO: 3)
5'-aactcgagttgtgaatgtgagttatgcg-3'

VP16-1F:
                                        (SEQ ID NO: 4)
5'-acggctccaccgaccgacgtc-3'

VP16-1RC:
                                        (SEQ ID NO: 5)
5'-ctacccaccgtactcgtcaattc-3'
```

```
VP16-2F:
                                            (SEQ ID NO: 6)
5'-ggacgaactccacttagacgg-3'

VP16-2RC:
                                            (SEQ ID NO: 7)
5'-ccgtctaagtggagttcgtcc-3'

VP16-3F:
                                            (SEQ ID NO: 8)
5'-tactcgagtcaacggctccaccgaccgacgt-3'

VP16-3RC:
                                            (SEQ ID NO: 9)
5'-aagagctcttacccaccgtactcgtcaattccaag-3'
```

(2) Construction of sGFP Gene Expression Cassettes

An sGFP gene was cut out from plasmid CaMV35S-sGFP (S65T)-NOS3' ("Experimental Protocol Viewing Plant Cells", under the editorship of Fukuda Hiroo et al, 1997, published by Shujunsha Co., Ltd., ISBN 4-87962-170-6), which was replaced by a GUS gene of pBI221 using adapters (NS-1F, NS-1RC) to prepare p35S-sGFP. A region from −830 bp to −91 bp of a CaMV35S promoter contained in p35S-sGFP was replaced by synthetic oligonucleotides (MRE-1F, MRE-1RC) to prepare pMRE/35S(−90)-sGFP.

pMRE/35S(−90)-sGFP was treated with a restriction enzyme EcoRV, and then dephoshorylated with "Calf intestine Alkaline Phosphatase" (Takara Bio, Inc.). Blunt-ended and phosphorylated synthetic oligonucleotides (MRE-1F, MRE-1RC) were inserted thereto using "Blunting Kination Ligation kit" (Takara Bio, Inc.) to arrange MRE sequences repeatedly twice in a forward direction. The twice repeated part of the MRE sequences thus obtained was cut out, which was blunted in the same way as described above, and once again, inserted in the EcoRV site, thereby preparing pMRE4/35S(−90)-sGFP in which the MRE sequences were repeatedly arranged 4 times in a forward direction.

Further, by using pBI221 as a template, a DNA fragment including a region from −46 bp to −1 bp of a CaMV35S promoter was amplified by PCR using two kinds of specific primers (46 bp-1F, 46 bp-1RC). The amplified DNA fragment was replaced by a region from −90 bp to −1 bp of the CaMV35S promoter located downstream from the MRE sequences repeatedly arranged 4 times in pMRE4/35S(−90)-sGFP to prepare pMRE4/35S(−46)-sGFP.

On the other hand, the DNA fragment was replaced with a sequence to which mutation was introduced into an as-1 site present in a region from −90 bp to −1 bp of the CaMV35S promoter (Benfey P N & Chua N H, 1990, Science 250, 959-966).

First, a genome DNA was extracted from the recombinant *Arabidopsis* seed (No. N70016) purchased from NASC. By using the extracted genome DNA as a template, PCR was carried out using two kinds of specific primers (90m-1F, 90m-1RC) so that a 35S(−90m) sequence having mutation at an as-1 site was TA-cloned into pCR2.1 (Invitrogen) to prepare pCR2.1-35S(−90m). By using the pCR2.1-35S(−90m) as a template, PCR was carried out using two kinds of specific primers (90m-2F, 90m-2RC) to add EcoRV site to the 5'-terminal and XbaI site to the 3'-terminal. The obtained DNA fragment was replaced with a region from −90 bp to −1 bp of the CaMV35S promoter located downstream from the MRE sequences repeatedly arranged 4 times in pMRE4/35S(−90)-sGFP to prepare pMRE4/35S(−90m)-sGFP.

In addition, by using a plasmid piL.erG3 (Tamai A et al, 2001, Mol Plant Microbe Interact 14(2), 126-134) as a template, PCR was carried out using two kinds of specific primers (71 bp-1F, 71 bp-1RC) to amplify a 5'-untranslated region (To71 sequence) of a 130 k/180 k gene of tomato mosaic virus. The amplified 5'-untranslated region sequence was inserted in an upstream from each sGFP structural gene of pMRE4/35S(−46)-sGFP and pMRE4/35S(−90m)-sGFP to prepare pMRE4/35S(−46)-To71sGFP and pMRE4/35S(−90m)-To71sGFP.

```
NS-1F:
                                            (SEQ ID NO: 10)
5'-ggccgcgagctcagt-3'

NS-1RC:
                                            (SEQ ID NO: 11)
5'-gactgagctcgc-3'

MRE-1F:
                                            (SEQ ID NO: 12)
5'-agcttagcgatgcgtcttttccgctgaaccgttccagcaaaaaag
actagat-3'

MRE-1RC:
                                            (SEQ ID NO: 13)
5'-atctagtctttttttgctggaacggttcagcggaaaagacgcatcg
cta-3', 46bp-1F:
                                            (SEQ ID NO: 14)
5'-tagatatcgcaagacccttcctctatataagg-3'

46bp-1RC:
                                            (SEQ ID NO: 15)
5'-atcctctagagtcccccgtgttc-3'

90m-1F:
                                            (SEQ ID NO: 16)
5'-gctatgaccatgattacgccaagcttg-3'

90m-1RC:
                                            (SEQ ID NO: 17)
5'-cattgttatatctccttggatccgtcg-3'

90m-2F:
                                            (SEQ ID NO: 18)
5'-tagatatctccacgtccataagggac-3'

90m-2RC:
                                            (SEQ ID NO: 19)
5'-aatctagactgcaggtcgtcctctcca-3'

71bp-1F:
                                            (SEQ ID NO: 20)
5'-tgtctagagtattttttacaacaattaccaacaac-3'

71bp-1RC:
                                            (SEQ ID NO: 21)
5'-aaggatcctgtagttgtagaatgtaaaatgtaatg-3'
```

(3) Linking Between Transcription Factor Gene Expression Cassettes and sGFP Gene Expression Cassettes p35S-ACE1-CR and p35S-ACE1/VP16AD-CR containing transcription factor gene expression cassettes were treated with restriction enzymes HindIII and EcoRI, and the respective transcription factor gene expression cassettes were cut out.

After pMRE/35S(−90)-sGFP, pMRE4/35S(−46)-sGFP, pMRE4/35S(−46)-To71sGFP and pMRE4/35S(−90m)-To71sGFP containing sGFP gene expression cassettes were treated with the restriction enzyme HindIII, blunt end formation and phosphorylation were carried out using "Blunting Kination Ligation kit", synthetic oligonucleotides (KXS-1F, KXS-1RC) were inserted therein to prepare pKXS-MRE/35S(−90)-sGFP and pKXS-MRE4/35S(−46)-sGFP, pKXS-MRE4/35S(−46)-To71sGFP, and pKXS-MRE4/35S(−90m)-To71sGFP. These plasmids prepared were treated with restriction enzymes KpnI and EcoRI, and the respective sGFP gene expression cassettes were cut out.

On the other hand, a GUS gene expression cassette contained in pBI121 (Clontech) was replaced by synthetic oligonucleotides (HEK-1, HEK-1RC) to prepare pBI121-HEK. The pBI121-HEK was treated with restriction enzymes HindIII and KpnI.

The transcription factor gene expression cassettes cut out and sGFP gene expression cassettes cut out were ligated to the pBI121-HEK treated with the restriction enzymes HindIII and KpnI to obtain vectors in which the transcription factor gene expression cassettes and sGFP gene expression cassettes were linked at respective terminator sides (see FIG. 1). A vector derived from p35S-ACE1-CR and pKXS-MRE/35S(−90)-sGFP was referred to as vector A. A vector derived from p35S-ACE1-CR and pKXS-MRE4/35S(−46)-sGFP was referred to as vector B. A vector derived from p35S-ACE1/VP16AD-CR and pKXS-MRE/35S(−46)-sGFP was referred to as vector C. A vector derived from p35S-ACE1/VP16AD-CR and pKXS-MRE4/35S(−46)-To71sGFP was referred to as vector D. A vector derived from p35S-ACE1/VP16AD-CR and pKXS-MRE/35S(−90m)-To71sGFP was referred to as vector E.

```
KXS-1F:
                                            (SEQ ID NO: 22)
5'-ggtacctcgagtcgac-3'

KXS-1RC:
                                            (SEQ ID NO: 23)
5'-gtcgactcgaggtacc-3'

HEK-1F:
                                            (SEQ ID NO: 24)
5'-agcttgaattcgtcgacggtacctaggacgagctc-3'

HEK-1RC:
                                            (SEQ ID NO: 25)
5'-aattgagctcgtcctaggtaccgtcgacgaattca-3'
```

Example 2

Expression Level Analysis of sGFP in Recombinant *Arabidopsis*

(1) Preparation and Selection of Recombinant *Arabidopsis*

Each of vectors A to E produced in Example 1 was introduced in *Agrobacterium* (*Agrobacterium tumefaciens* strain C58C1), respectively. The obtained *Agrobacterium* was cultured in an LB agar medium (0.5% yeast extract, 1.0% Bactotriptone, 0.5% sodium chloride, 1% agar) containing 50 mg/L of kanamycin, 100 mg/L of ampicillin and 100 mg/L of rifampicin, and a drug-resistant colony was selected to obtain recombinant *Agrobacterium*. *Arabidopsis* (*Arabidopsis thaliana* ecotype Columbia) was infected by the obtained recombinant Agrobacterium according to the method described in Model Plant Laboratory Manual (edited by Iwabuchi Masaki et al, 2000, Springer-Verlag Tokyo Co., Ltd., ISBN 4-431-70881-2 C3045) to introduce genes. After $T_1$ seeds collected from the *Arabidopsis* subjected to gene introduction, seeds were sowed and grown on a modified MS agar medium (MS inorganic salts, B5 vitamin, 1% sucrose, 0.8% agar) containing 20 mg/L of Benlate, 200 mg/L of Claforan, 25 mg/L kanamycin to select a plant individual resistant to kanamycin. The selected plant individual was transplanted to a pot in which culture soil was previously placed, and grown in an artificial weather container to obtain $T_2$ seeds. After the obtained $T_2$ seeds were sowed and grown on a modified MS agar medium (MS inorganic salts, B5 vitamin, 2% sucrose, 0.8% agar) containing 25 mg/L kanamycin, a plant line in which plant individuals having resistance to kanamycin appeared in a ratio of 3:1 at a significant level of 5% based on a $\chi^2$ test was selected. The culture conditions of growing plant individuals were such that the light period was 23 hours, the dark period was 1 hour and a temperature was 23 to 25° C.

(2) Expression Level Analysis of sGFP by Real-Time PCR

Regarding the selected plant lines, 6 plant individuals of 10 days after sowing were transplanted onto a modified MS agar medium (MS inorganic salts, B5 vitamin, 2% sucrose, 0.8% agar) containing 100 μM $CuSO_4$ as an induced expression treatment group to carry out a treatment for induced expression of a target foreign gene by copper ions (hereinafter, sometimes, referred to as the induced expression treatment). Additionally, as a non-induced expression treatment group, a modified MS agar medium not containing $CuSO_4$ was used.

Then, from the plant individuals after the induced expression treatment of 6 hours, whole RNA was extracted using a plant RNA extracting kit "RNeasy Plant Mini Kit" (QIAGEN). From the extracted whole RNA, cDNA was synthesized using a cDNA synthesis kit "ReverTra Ace" (TOYOBO). By using the synthesized cDNA as a template, the quantitative determination of the mRNA amount was carried out by real-time PCR using a 7500 Fast Real-time PCR apparatus (Applied Biosystems). For the quantitative determination of the mRNA amount of an sGFP gene, two kinds of specific primers (S01F, S01R) and TaqMan probe (S01) were used. As an internal standard, an *Arabidopsis* actin gene (AtACT2, GenBank Accession Number NM180280) was used. For the quantitative determination of the mRNA amount of an AtACT gene, two kinds of specific primers (S03F, S03R) and TaqMan probe (S03) were used.

```
S01F:
5'-tccgccctgagcaaagac-3'          (SEQ ID NO: 26)

S01R:
5'-gaactccagcaggaccatgtg-3'       (SEQ ID NO: 27)

S01:
5'-FAM-ccaacgagaagcgcga-MGB-3'    (SEQ ID NO: 28)

S03F:
5'-cggtggttccattcttgctt-3'        (SEQ ID NO: 29)

S03R:
5'-cggccttggagatccacat-3'         (SEQ ID NO: 30)

S03:
5'-VIC-cctcagcacattcc-MGB-3'      (SEQ ID NO: 31)
```

As a result, regarding the recombinant *Arabidopsis* into which vector A was introduced, the mRNA amount of the sGFP gene in the induced expression treatment group was 4.6-fold as much as the mRNA amount of the sGFP gene in the non-induced expression treatment group (hereinafter, sometimes, referred to as the induction ratio in the recombinant *Arabidopsis* into which vector A was introduced). Regarding the recombinant *Arabidopsis* into which vector B where the MRE sequences was repeatedly arranged 4 times with shortened CaMV35S promoter from −90 bp to −46 bp was introduced, the mRNA amount of the sGFP gene in the induced expression treatment group was 8.6-fold as much as the mRNA amount of the sGFP gene in the non-inducible expression treatment group (hereinafter, sometimes, referred to as the induction ratio in the recombinant *Arabidopsis* into which vector B was introduced), and 1.9-fold improvement was confirmed as compared with the induction ratio of the recombinant *Arabidopsis* into which vector A was introduced.

On the other hand, regarding the recombinant *Arabidopsis* into which vector C where VP16AD was added to ACE1 transcription factor was introduced, the mRNA amount of the sGFP gene in the induced expression treatment group was 273.0-fold as much as the mRNA amount of the sGFP gene in the non-induced expression treatment group (hereinafter, sometimes, referred to as the induction ratio in the recombinant *Arabidopsis* into which vector C was introduced), and 31.7-fold improvement was confirmed as compared with the induction ratio in the recombinant *Arabidopsis* into which vector B was introduced.

Further, regarding the recombinant *Arabidopsis* into which vector D where the 5'-untranslated region sequence of a 130 k/180 k gene of a tomato mosaic virus was inserted was introduced, the mRNA amount of the sGFP gene in the induced expression treatment group was 628.6-fold as much as the mRNA amount of the sGFP gene in the non-induced expression treatment group (hereinafter, sometimes, referred to as the induction ratio in the recombinant *Arabidopsis* into which vector D was introduced), and 2.3-fold improvement was confirmed as compared with the induction ratio in the recombinant *Arabidopsis* into which vector C was introduced.

Figure 2:
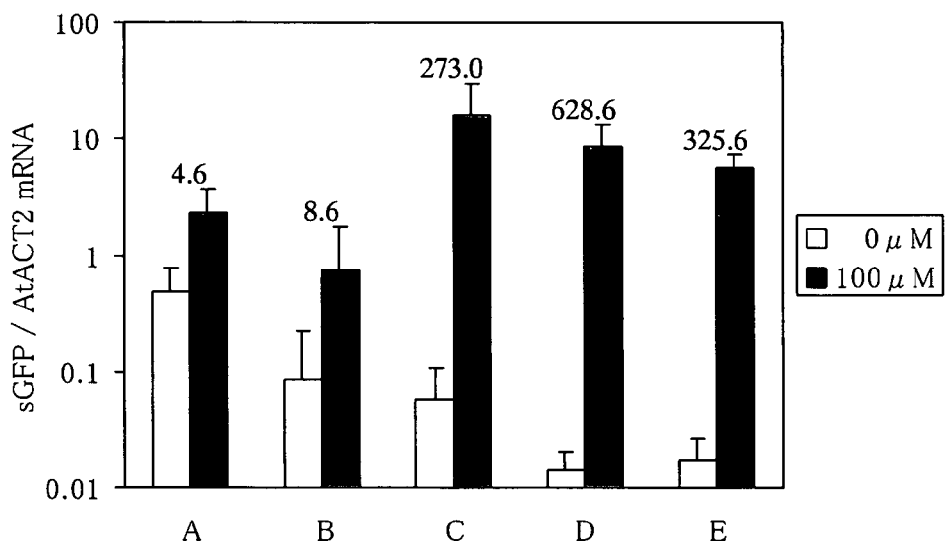
FIG. 2 is a graph showing the results obtained by determination of the mRNA amount of an sGFP gene with a real-time PCR in a recombinant *Arabidopsis* to which a copper ion-inducible sGFP gene expression vector has been introduced. The numeric value in the graph shows a ratio of the mRNA amount of an sGFP gene in an induced expression treatment group to the mRNA amount of an sGFP gene in a non-induced expression treatment group.

Further, regarding the recombinant *Arabidopsis* into which vector E where 35S (−90m) sequence having mutation at the as-1 site was used was introduced, the mRNA amount of the sGFP gene in the induced expression treatment group was 325.6-fold as much as the mRNA amount of the sGFP gene in the non-inducible expression treatment group (hereinafter, sometimes, referred to as the induction ratio in the recombinant *Arabidopsis* into which vector E was introduced) (see FIG. 2).

Example 3

Expression Level Analysis of sGFP in Recombinant Tobacco (1) Preparation and Selection of Recombinant Tobacco Vectors B and E produced in Example 1 were introduced into *Agrobacterium* (*Agrobacterium tumefaciens* strain LBA4404), respectively. The obtained *Agrobacterium* was cultured in an LB agar medium (0.5% yeast extract, 1.0% Bactotriptone, 0.5% sodium chloride, 1% agar) containing 50 mg/L of kanamycin, 300 mg/L of streptomycin and 100 mg/L of rifampicin, and a drug-resistant colony was selected to obtain recombinant *Agrobacterium*. Tobacco (Nicotiana tabacum strain SR1) was infected by the obtained recombinant *Agrobacterium* according to the method described in Plant Gene Manipulation Manual (written by Uchimiya Hirofumi, 1992, Kodansha Scientific Corporation) to introduce genes. From the tobacco leaves subjected to gene introduction, adventitious buds showing resistance to kanamycin of 100 mg/L were selected, and plant individuals were regenerated from the selected adventitious buds. After $T_1$ seeds collected from the obtained plant individual, seeds were sowed and grown on a MS agar medium (MS inorganic salts, MS vitamin, 3% sucrose, 0.8% agar) containing 50 mg/L of kanamycin, a plant line in which plant individuals showing resistance to kanamycin appeared in a ratio of 3:1 at a significant level of 5% based on a $\chi^2$ test was selected. The culture conditions of growing plant individuals were such that the light period was 23 hours, the dark period was 1 hour and a temperature was 23 to 25° C.

(2) Expression Level Analysis of sGFP by Real-Time PCR

Regarding the selected plant lines, 3 plant individuals of 12 days after sowing were transplanted onto a MS agar medium (MS inorganic salts, MS vitamin, 3% sucrose, 0.8% agar) containing 100 μM $CuSO_4$ as an induced expression treatment group to carry out induced expression of a target foreign gene by copper ion (hereinafter, sometimes, referred to as the induced expression treatment). Additionally, as a non-inducible expression treatment group, a MS agar medium not containing $CuSO_4$ was used.

Then, from the plant individual 6 hours after the inducible expression treatment, whole RNA was extracted using a plant RNA extracting kit "RNeasy Plant Mini Kit" (QIAGEN). From the extracted whole RNA, cDNA was synthesized using a cDNA synthesis kit "ReverTra Ace" (TOYOBO). By using the synthesized cDNA as a template, the quantitative determination of the mRNA amount was carried out by real-time PCR using a 7500 Fast Real-time PCR apparatus (Applied Biosystems). For the quantitative determination of the mRNA amount of an sGFP gene, two kinds of specific primers (S01F, S01R) and TaqMan probe (S01) were used. As an internal standard, a tobacco ubiquitin gene (NtUBI, GenBank Accession Number U66264) was used. For the quantitative determination of the mRNA amount of an NtUBI gene, two kinds of specific primers (S06F, S06R) and TaqMan probe (S06) were used.

```
S06F:
5'-gaagcagctcgaggatggaa-3'           (SEQ ID NO: 32)

S06R:
5'-gacgggttgactctttctggat-3'         (SEQ ID NO: 33)

S06:
5'-VIC-accttggctgactacaa-MGB-3'      (SEQ ID NO: 34)
```

As a result, regarding the recombinant tobacco into which vector B was introduced, the mRNA amount of the sGFP gene in the induced expression treatment group was 9.6-fold as much as the mRNA amount of the sGFP gene in the non-inducible expression treatment group (hereinafter, sometimes, referred to the induction ratio in the recombinant tobacco into which vector B was introduced).

Figure 3:
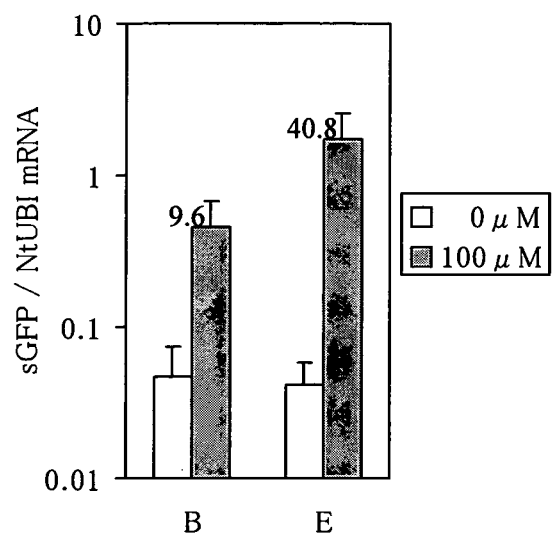
FIG. 3 is a graph showing the results obtained by determination of the mRNA amount of an sGFP gene with a real-time PCR in a recombinant tobacco to which a copper ion-inducible sGFP gene expression vector has been introduced. The numeric value in the graph shows a ratio of the mRNA amount of an sGFP gene in an induced expression treatment group to the mRNA amount of an sGFP gene in a non-inducible expression treatment group.

On the other hand, regarding the recombinant tobacco into which vector E where VP16AD was added to an ACE1 transcription factor and a 5'-untranslated region sequence of a 130 k/180 k gene of a tomato mosaic virus was inserted in upstream from an sGFP structural gene was introduced, the mRNA amount of the sGFP gene in the induced expression treatment group was 40.8-fold as much as the mRNA amount of the sGFP gene in the non-inducible expression treatment group (hereinafter, sometimes, referred to as the induction ratio in the recombinant tobacco into which vector E was introduced), and 4.2-fold improvement was confirmed as compared with the induction ratio in the recombinant tobacco into which vector B was introduced (see FIG. 3).

Example 4

Accumulation Level Analysis of GFP in Recombinant Tobacco Cultured Cells (1) Preparation and Selection of Recombinant Tobacco Cultured Cells Each of vectors A, B and E produced in Example 1 was introduced into tobacco cultured cells (BY-2) by using gold particles of 1.0 μm in diameter coated with each of these vectors according to a particle gun method (Morikawa Hiromichi et al, 1992, Plant Cell Engineering, Vol. 4 No. 1 p. 47-52, Shujunsha Co., Ltd.). The DNA amount per 1.0 mg of gold particles was adjusted to 0.1 μg. On the 3rd to 5th days after gene introduction operation, the tobacco cell suspension cultures subjected to gene introduction were spread on a modified MS agar medium (MS inorganic salts, 3% sucrose, 1 µM 2,4-D, 1 mg/L thiamin HCl, 100 mg/L myo-inositol, 200 mg/L $KH_2PO_4$, 0.8% agar) containing 30 mg/L of kanamycin. After one month of culture, a cell mass showing resistance to 30 mg/L kanamycin was selected, and the selected cell masses were cultured for 4 to 8 weeks while subculturing in a new agar medium every 1 to 2 weeks. The culture was carried out under dark conditions at 23 to 25° C.

(2) Accumulation Level Analysis of GFP by Fluorescence Plate Reader

The obtained cell mass was transplanted onto modified MS agar medium (MS inorganic salts, 3% sucrose, 1 µM 2,4-D, 1 mg/L thiamin HCl, 100 mg/L myo-inositol, 200 mg/L $KH_2PO_4$, 0.8% agar) containing 100 µM $CuSO_4$ as an inducible expression treatment group to carry out a treatment for induced expression of a target foreign gene by copper ion (hereinafter, sometimes, referred to as the induced expression treatment). Additionally, as a non-inducible expression treatment group, a modified MS agar medium not containing $CuSO_4$ was used.

Then, regarding the cell mass of 3 days after the induced expression treatment, the fluorescence emission state of GFP was examined by a fluorescence microscope (Nikon).

The cell mass whose increase in fluorescence emission was observed was frozen with liquid nitrogen. Then, glass beads (0.25 to 0.5 mm) and extraction buffer (1×PBS(−), 5 mM DTT, 1 mM PMSF, 0.1% protease inhibitor cocktail) were added to the frozen material, and ground by a grinding apparatus "Mixermill" (QIAGEN). After the obtained ground product was centrifuged at 15000 rpm, 4° C. for 5 minutes by a table centrifugal machine to recover a supernatant, the resulting supernatant obtained was used as a protein extraction solution. Next, the protein extraction solution was appropriately diluted with 1×PBS(−), and the diluted solution was subjected to measurement of fluorescence intensity using a Multilabel counter "wallac 1420 ARVOMX" (Perkin-Elmer). As a standard sample, a diluted solution obtained by diluting recombinant GFP (Cosmo Bio) with 1×PBS(−) was used. A GFP converted amount per an amount of a soluble protein was calculated from the fluorescence intensity measured, from which a corresponding value of a control wild-type cell mass as a background value was subtracted to calculate an accumulation level of GFP. The concentration of the protein in the protein extraction solution was quantitatively determined by a Bradford method.

As a result, regarding the recombinant tobacco cultured cells into which vector A was introduced, the accumulation level of GFP in the induced expression treatment group was 1.6-fold as much as the accumulation level of GFP in the non-inducible expression treatment group (hereinafter, sometimes, referred to as the induction ratio in the recombinant tobacco cultured cells into which vector A was introduced). Regarding the recombinant tobacco cultured cells into which vector B where the MRE sequences were repeatedly arranged 4 times with shortened CaMV35S promoter from −90 bp to −46 bp was introduced, the accumulation level of GFP in the induced expression treatment group was 1.9-fold as much as the accumulation level of GFP in the non-inducible expression treatment group (hereinafter, sometimes, referred to as the induction ratio in the recombinant tobacco cultured cells into which vector B was introduced).

Figure 4:
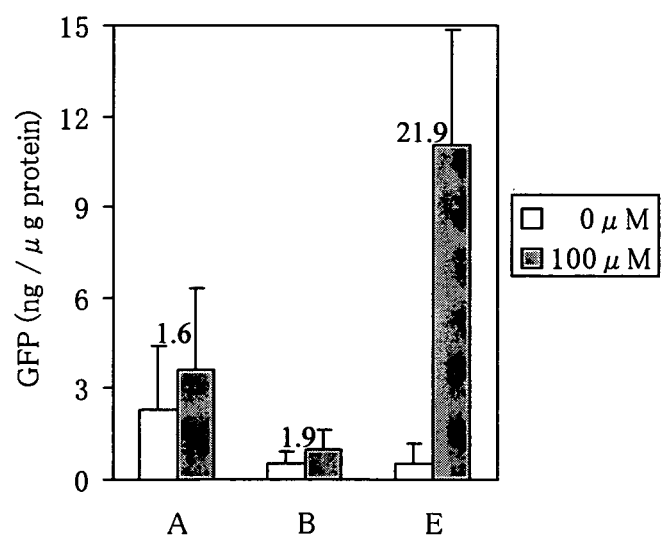
FIG. 4 is a graph showing the results obtained by determination of an accumulation level of GFP (in terms of a GFP accumulation level calculated from fluorescence intensity of GFP) in recombinant tobacco cultured cells to which a copper ion-inducible sGFP gene expression vector has been introduced. The numeric value in the graph shows a ratio of an accumulation level of GFP in an induced expression treatment group to an accumulation level of GFP in a non-inducible expression treatment group.

On the other hand, regarding the recombinant tobacco cultured cells into which vector E where VP16AD was added to an ACE1 transcription factor and a 5'-untranslated region sequence of a 130 k/180 k gene of a tomato mosaic virus was inserted in upstream from sGFP gene was introduced, the accumulation level of GFP in the inducible expression treatment group was 21.9-fold as much as the accumulation level of GFP in the non-inducible expression treatment group (hereinafter, sometimes, referred to as the induction ratio in the recombinant tobacco cultured cells into which vector E was introduced), and 11.5-fold improvement was confirmed as compared with the induction ratio in the recombinant tobacco cultured cells into which vector B was introduced (see FIG. 4).

Example 5

Transient Assay of Induced Expression System (1) Preparation of Samples, and Gene Introduction by Particle Gun The respective leaves of Arabidopsis (*Arabidopsis thaliana*), tobacco (*Nicotiana tabacum*), soybean (*Glycine max* 'Jack'), carnation (*Dianthus caryophyllus* 'True Love', Kilin Green and Flower Corp.), rice (*Oryza sativa* ssp japonica cv Nipponbare) and Tiger lily (*Liliunm lancifolium*) were cut out, and the leaves (leaf disc) were placed on a 0.6% agar medium containing 100 µM $CuSO_4$ as the induced expression treatment group to carry out a treatment of induced expression of a target foreign gene by copper ion (hereinafter, sometimes, referred to as the induced expression treatment). As a non-inducible expression treatment group, a 0.6% agar medium not containing $CuSO_4$ was used.

Then, a composition obtained by mixing equal amounts of vector E produced in Example 1 and pBI221 (Clontech) was introduced into the leaf disc 1 day after the induced expression treatment by a particle gun method using gold particles of 1.0 µm in diameter coated with the above-described composition. The DNA amount per 1.0 mg of gold particles was adjusted to 0.1 µg. pBI221 was mixed in order to correct the efficiency of gene introduction. As a control, in place of the above-described composition, a composition obtained by mixing equal amounts of p35S-sGFP produced in Example 1 and pBI221 was used.

(2) Transient Expression Analysis of Reporter Genes

Regarding the leaf disc into which genes were introduced, the number of spots where fluorescence emission of GFP was observed was counted by a fluorescence microscope (Nikon) 1 day after gene introduction. Then, the leaf disc that genes were introduced was immersed in a GUS stain solution (0.5 mg/ml X-Gluc, 0.5 mM $K_3Fe(CN)_6$, 0.5 mM $K_4Fe(CN)_6$, 0.01% Triton X-100, 100 mM sodium phosphate), which was subjected to vacuum treatment at 400 mmHg for 10 minutes, followed by staining at 37° C. for 1 day. The leaf disc stained was decolored with 70% ethanol, then, the number of spots where GUS stain was observed was counted by a microscope (Nikon).

As a result, in the leaf disc into which p35S-sGFP was introduced, there was no significant difference in the number of spots due to GFP fluorescence between the induced expression treatment group and the non-induced expression treatment group. On the other hand, in the leaf disc into which vector E was introduced, the number of spots due to GFP fluorescence in the induced expression treatment group observed was larger as compared with that of spots due to GFP fluorescence in the non-induced expression treatment group. The number of spots resulted from GUS stain was stably observed in either of the treatment groups, so that it was confirmed that there was no large difference in gene introduction efficiency (see Table 1).

TABLE 1

| Object plant | Introduced gene | Copper ion concentration (μM) | Number of spots by GFP fluorescence | Number of spots by GUS stain | Leaf disc tested (piece) |
|---|---|---|---|---|---|
| Arabidopsis | E, pBI221 | 0 | 0 | 108 | 4 |
|  |  | 100 | 25 | 50 | 4 |
|  | p35S-sGFP, PBI221 | 0 | 31 | 86 | 4 |
|  |  | 100 | 42 | 62 | 4 |
| Tobacco | E, pBI221 | 0 | 13 | 63 | 7 |
|  |  | 100 | 579 | 118 | 7 |
|  | p35S-sGFP, pBI221 | 0 | 567 | 99 | 7 |
|  |  | 100 | 476 | 41 | 7 |
| Soybean | E, pBI221 | 0 | 6 | 248 | 4 |
|  |  | 100 | 75 | 216 | 4 |
|  | p35S-sGFP, pBI221 | 0 | 307 | 187 | 4 |
|  |  | 100 | 277 | 136 | 4 |
| Carnation | E, pBI221 | 0 | 3 | 61 | 7 |
|  |  | 100 | 76 | 25 | 7 |
|  | p35S-sGFP, pBI221 | 0 | 57 | 19 | 8 |
|  |  | 100 | 68 | 5 | 8 |
| Rice | E, pBI221 | 0 | 17 | 12 | 11 |
|  |  | 100 | 76 | 14 | 11 |
|  | p35S-sGFP, pBI221 | 0 | 80 | 7 | 11 |
|  |  | 100 | 104 | 3 | 11 |
| Tiger lily | E, pBI221 | 0 | 2 | 15 | 7 |
|  |  | 100 | 40 | 10 | 7 |
|  | p35S-sGFP, pBI221 | 0 | 196 | 4 | 7 |
|  |  | 100 | 178 | 1 | 7 |

Example 6

Induction of Flowering of Recombinant *Arabidopsis*

(1) Preparation of an Introduction Vector

Figure 5:
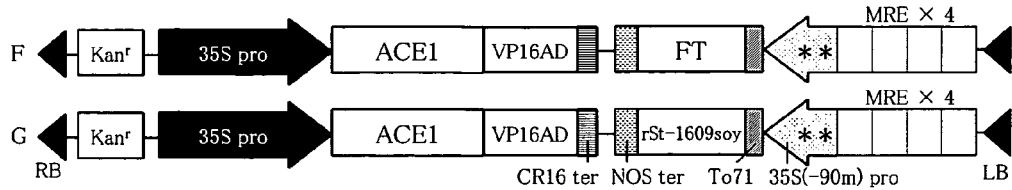
FIG. 5 is a schematic view illustrating the structures in T-DNA regions of a copper ion-inducible FT gene expression vector and an inducible rSt-1609soy gene expression vector. The symbol "*" in FIG. 5 shows a mutation-introduced region in the as-1 site.

*Arabidopsis* (*Arabidopsis thaliana* ecotype Columbia) was sowed on a modified MS agar medium (MS inorganic salts, B5 vitamin, 2% sucrose, 0.8% agar) and grown at 23° C. for 3 weeks. The resulting plant was transplanted to a pot in which culture soil was previously placed, and grown in an artificial weather container. From the flower bud and true leaf of 2 weeks after transplantation, whole RNA was extracted using a plant RNA extracting kit "RNeasy Plant Mini Kit" (QIAGEN). From the extracted whole RNA, cDNA was synthesized using a cDNA synthesis kit "ReverTra Ace" (TOYOBO). By using the synthesized cDNA as a template, a FT gene (GenBank Accession Number AB027504) was amplified by PCR using 2 kinds of specific primers (FT-1F, FT-1RC). The amplified FT gene was replaced by a GUS gene of pBI221 (Clontech). By using the thus obtained plasmid as a template, fusion PCR was carried out using 6 kinds of specific primers (FT-2F, FT-2RC, FT-3F, FT-3RC, FT-4F, FT-1RC), mutation not accompanied with amino acid substitution was introduced at a BamHI site and an EcoRI site present in the FT gene, and an XbaI site at 5' terminal was replaced with the BamHI site. The thus obtained modified FT gene was replaced with the sGFP gene of pKXS-MRE4/35S (−90m)-To71sGFP prepared in Example 1 to prepare pKXS-MRE4/35S(−90m)-To71FT. According to the same method as that described in Example 1, vector F was obtained by the FT gene expression cassette contained in pKXS-MRE4/35S (−90m)-To71FT and a transcription factor gene expression cassette contained in p35S-ACE1/VP16AD-CR were linked at the terminator sides (see FIG. 5).

FT-1F:
                              (SEQ ID NO: 35)
5'-taatctagaatgtctataaatataagagaccctc-3'

FT-1RC:
                              (SEQ ID NO: 36)
5'-atagagctcctaaagtcttcttcctccg-3'

FT-2F:
                              (SEQ ID NO: 37)
5'-taaggatccatgtctataaatataagagaccctc-3'

FT-2RC:
                              (SEQ ID NO: 38)
5'-gaacatctggatcgaccataaccaaagta-3'

FT-3F:
                              (SEQ ID NO: 39)
5'-tactttggttatggtcgatccagatgttc-3'

FT-3RC:
                              (SEQ ID NO: 40)
5'-gacacgatgaatacctgcagtggga-3'

FT-4F:
                              (SEQ ID NO: 41)
5'-tcccactgcaggtattcatcgtgtc-3'

(2) Preparation and Selection of Recombinant *Arabidopsis*, and Induction of Flowering Vector F produced was introduced into *Agrobacterium* (*Agrobacterium tumefaciens* strain C58C1). The obtained *Agrobacterium* was cultured in an LB agar medium (0.5% yeast extract, 1.0% Bactotriptone, 0.5% sodium chloride, 1% agar) containing 50 mg/L of kanamycin, 100 mg/L of ampicillin and 100 mg/L of rifampicin, and a drug-resistant colony was selected to obtain recombinant *Agrobacterium*. *Arabidopsis* (*Arabidopsis thaliana* ecotype Columbia) was infected by the obtained recombinant *Agrobacterium* according to the method described in Model Plant Laboratory Manual (edited by Iwabuchi Masaki et al, 2000, Springer-Verlag Corporation, ISBN 4-431-70881-2 C3045) to introduce genes. After $T_1$ seeds collected from the *Arabidopsis* subjected to gene introduction, seeds were sowed and grown on a modified MS agar medium (MS inorganic salts, B5 vitamin, 1% sucrose, 0.8% agar) including 20 mg/L of Benlate, 200 mg/L of Claforan, 25 mg/L kanamycin, plant individuals resistant to kanamycin were selected. The selected plant individuals were transplanted to a pot in which culture soil was previously placed, grown in an artificial weather container to obtain $T_2$ seeds. After the obtained $T_2$ seeds were sowed and grown on a modified MS agar medium (MS inorganic salts, B5 vitamin, 2% sucrose, 0.8% agar) containing 25 mg/L kanamycin, a plant line in which plant individuals having resistance to kanamycin appeared in a ratio of 3:1 at a significant level of 5% based on $\chi^2$ test was selected. Plant individuals of the selected lines were transplanted to pods in which culture soil was previously placed and grown in an artificial weather container to obtain $T_3$ seeds. The obtained $T_3$ seeds were sowed on a modified MS agar medium (MS inorganic salts, B5 vitamin, 2% sucrose, 0.8% agar) containing 25 mg/L kanamycin, and grown. Then, a homozygote that all showed resistance to kanamycin was selected. The culture conditions of growing plant individuals were such that the light period was 23 hours, dark period was 1 hour and a temperature was 23 to 25° C.

Regarding the homozygote selected, $T_3$ seeds were sowed on a modified MS agar medium (MS inorganic salts, B5 vitamin, 2% sucrose, 0.8% agar). After they were grown under conditions of the light period of 23 hours, the dark period of 1 hour and a temperature at 23 to 25° C. for 3 days, they were further grown under conditions of the light period of 12 hours, the dark period of 12 hours and a temperature at 23 to 25° C. The plant individuals of 10 days after sowing were transplanted onto a modified MS agar medium (MS inorganic salts, B5 vitamin, 2% sucrose, 0.8% agar) containing 100 μM $CuSO_4$ as an induced expression treatment group to carry out a treatment for induced expression of a target foreign gene by copper ion (hereinafter, sometimes, referred to as the induced expression treatment). As a non-inducible expression treatment group, a modified MS agar medium not containing $CuSO_4$ was used.

Figure 6:
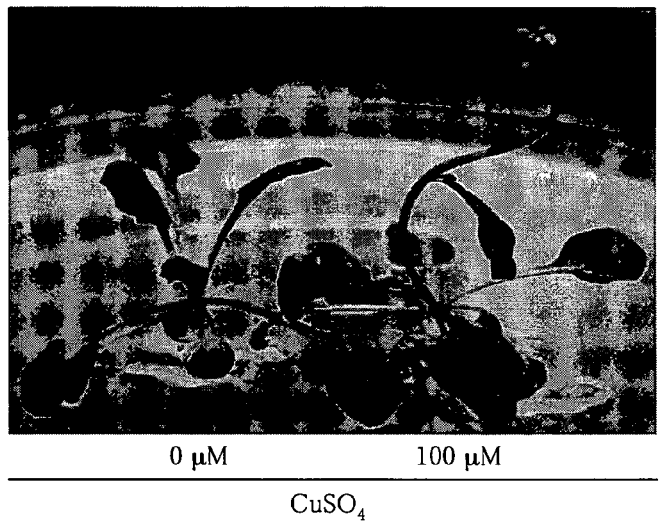
FIG. 6 is a view showing the difference in flowering time of a recombinant *Arabidopsis* to which a copper ion-inducible FT gene expression vector has been introduced.

The plant individuals after the induced expression treatment of 3 days (13 days after sowing) were transplanted onto a modified MS agar medium (MS inorganic salts, B5 vitamin, 2% sucrose, 0.8% agar) not containing 100 μM $CuSO_4$. The plant individuals in 11 days after the inducible expression treatment (24 days after sowing) were examined. As a result, in the induced expression treatment group, flowering was early induced as compared with that in the non-inducible expression treatment group (see FIG. 6).

Example 7

Induction of Herbicide-Resistance of Recombinant Tobacco (1) Preparation of an Introduction Vector An rSt-1609soy gene was cut out from pSUM-35S-rSt-1609soy (JP 2006-001921 A) by using restriction enzymes BamHI and SacI. The rSt-1609soy gene cut out was replaced by an sGFP gene of pKXS-MRE4/35S(−90m)-To71sGFP prepared in Example 1 to prepare pKXS-MRE4/35S(−90m)-To71rSt-1609soy. According to the same method as that described in Example 1, vector G was obtained by the rSt-1609soy gene expression cassette contained in pKXS-MRE4/35S(−90m)-To71rSt-1609soy and a transcription factor gene expression cassette contained in p35S-ACE1/VP16AD-CR were linked at the terminator sides (see FIG. 5).

(2) Preparation and Selection of Recombinant Tobacco, and Induction of Herbicide Resistance Vector G prepared was introduced to *Agrobacterium* (*Agrobacterium tumefaciens* strain LBA4404). The obtained *Agrobacterium* was cultured in an LB agar medium (0.5% yeast extract, 1.0% Bactotriptone, 0.5% sodium chloride, 1% agar) containing 50 mg/L of kanamycin, 300 mg/L of streptomycin and 100 mg/L of rifanpicin rifampicin, and a drug-resistant colony was selected to obtain recombinant Agrobacterium. Tobacco (Nicotiana tabacum strain SR1) was infected by the obtained recombinant Agrobacterium according to the method described in Plant Gene Manipulation Manual (written by Uchimiya Hirofumi, 1992, Kodansha Scientific Corporation) to introduce genes. From tobacco leaves subjected to gene introduction, adventitious bud showing resistance to kanamycin of 100 mg/L was selected, and a plant individual was regenerated from the selected adventitious bud. After $T_1$ seeds collected from the obtained plant individual were sowed and grown on a MS agar medium (MS inorganic salts, MS vitamin, 3% sucrose, 0.8% agar) containing 50 mg/L of kanamycin, a plant line in which plant individuals showing resistance to kanamycin appeared in a ratio of 3:1 at a significant level of 5% based on $\chi^2$ test was selected. The culture conditions of growing plant individuals were such that the light period was 23 hours, the dark period was 1 hour and a temperature was 23 to 25° C.

Regarding the selected plant lines, the plant individual of several days after sowing was transplanted to a pot in which culture soil was previously placed, then, to the plant individual, an aqueous solution containing $CuSO_4$ is sprayed as an induced expression treatment group. An aqueous solution not containing $CuSO_4$ was used as a non-inducible expression treatment group.

Further, to the above-described plant individual, a PPO inhibition type herbicide is sprayed.

In the induced expression treatment group, resistance to the herbicide with higher concentration is resulted as compared with the non-induced expression treatment group.

Example 8

Utilization of Other 5'-Untranslated Region Sequences (1) Preparation of Introduction Vectors By using pKXS-MRE4/35S(−46)-To71sGFP prepared in Example 1 as a template, PCR was carried out using 2 kinds of specific primers (EV46-1F, o46-1RC) to amplify 46o fragment. Further, by using a plasmid CaMV35S-sGFP(S65T)-NOS3' ("Experimental Protocol Viewing Plant Cell" under the editorship of Fukuda Hiroo et al, 1997, Shujunsha Co., Ltd., ISBN 4-87962-170-6) as a template, PCR was carried out using 2 kinds of specific primers (omg-1F, omg-1RC) to amplify an Ω sequence fragment. Furthermore, by using pKXS-MRE4/35S(−46)-To71sGFP prepared in Example 1 as a template, PCR was carried out using 2 kinds of specific primers (oGFP-1F, SlGFP-1RC) to amplify an oGFP fragment. By using the obtained three kinds of DNA fragments (46o, Ω sequence, oGFP) as templates, PCR was carried out using 2 kinds of specific primers (EV46-1F, SlGFP-1RC) to amplify an OsGFP fragment. The obtained OsGFP fragment was replaced by a fragment cut out at the EcoRV and SacI sites of pKXS-MRE4/35S(−46)-To71sGFP prepared in Example 1 to prepare pKXS-MRE4/35S(−46)-ΩsGFP. By using the prepared pKXS-MRE4/35S(−46)-ΩsGFP as a template, PCR was carried out using 2 kinds of specific primers (Xo-1F, SlGFP-1RC) to amplify an xΩsGFP fragment. The obtained xΩsGFP fragment was replaced by a fragment cut out at XbaI and SacI sites of pKXS-MRE4/35S(−46)-To71sGFP prepared in Example 1 to prepare pKXS-MRE4/35S (−46)-xΩs-GFP.

By using pKXS-MRE4/35S(−46)-To71sGFP prepared in Example 1 as a template, PCR was carried out using 2 kinds of specific primers (EV46-1F, a46-1RC) to amplify a 46a fragment. Further, by using pKXS-MRE4/35S(−46)-To71sGFP prepared in Example 1 as a template, PCR was carried out using 2 kinds of specific primers (aGFP-1F, SlGFP-1RC) to amplify an aGFP fragment. The obtained two kinds of DNA fragments (46a, aGFP) and synthetic oligonucleotide (A94-1F, A94-1RC) were mixed. By using this mixture as a template, PCR was carried out using 2 kinds of specific primers (EV46-1F, SlGFP-1RC) to amplify an A94sGFP fragment having a 5'-untranslated region sequence derived from an alcohol dehydrogenase gene of tobacco. The obtained A94sGFP fragment was replaced by a fragment cut out at EcoRV and SacI sites of pKXS-MRE4/35S(−46)-To71sGFP prepared in Example 1 to prepare pKXS-MRE4/35S(−46)-A94sGFP. By using the prepared pKXS-MRE4/35S(−46)-A94sGFP as a template, PCR was carried out using 2 kinds of specific primers (Xa-1F, SlGFP-1RC) to amplify xA94sGFP fragment. The obtained xA94sGFP fragment was replaced by a fragment cut out at XbaI and SacI sites of pKXS-MRE4/35S(−46)-To71sGFP prepared in Example 1 to prepare pKXS-MRE4/35S(−46)-xA94sGFP.

Figure 7:
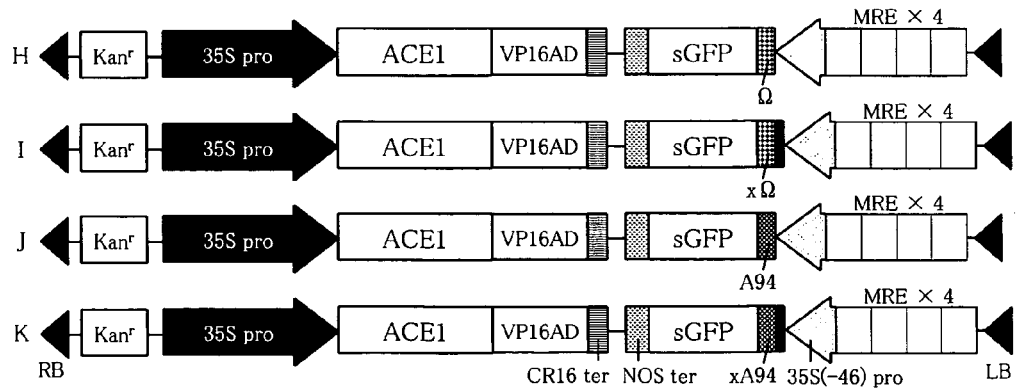
FIG. 7 is a schematic view illustrating the structures of T-DNA regions of copper ion-inducible sGFP gene expression vectors.

According to the same method as that described in Example 1, the four kinds of sGFP gene expression cassettes prepared and a transcription factor gene expression cassette contained in p35S-ACE1/VP16AD-CR were linked at terminator sides to obtain vectors (see FIG. 7). A vector derived from pKXS-MRE4/35S(−46)-ΩsGFP was referred to as vector H. A vector derived from pKXS-MRE4/35S(−46)-xΩs-GFP was referred to as vector I. A vector derived from pKXS-MRE4/35S(−46)-A94sGFP was referred to as vector J, and a vector derived from pKXS-MRE4/35S(−46)-xA94sGFP was referred to as vector K.

EV46-1F:
(SEQ ID NO: 42)
5'-ctagatatcgcaagacccttcctct-3' o46-1RC:
(SEQ ID NO: 43)
5'-gtaaaaatacctctccaaatgaaatgaacttc-3' omg-1F:
(SEQ ID NO: 44)
5'-ggtattttacaacaattaccaacaacaac-3' omg-1RC:
(SEQ ID NO: 45)
5'-cattgtaattgtaaatagtaattgtaatgt-3' oGFP-1F:
(SEQ ID NO: 46)
5'-acaattacaatggtgagcaagggcga-3'

SlGFP-1RC:
(SEQ ID NO: 47)
5'-ttagagctcttacttgtacagctcgtcc-3'

Xo-1F:
(SEQ ID NO: 48)
5'-gactctagagtattttacaacaattaccaac-3' a46-1RC:
(SEQ ID NO: 49)
5'-gttaaatagaccctctccaaatgaaatgaacttc-3' aGFP-1F:
(SEQ ID NO: 50)
5'-gaaaaataaatggtgagcaagggcgag-3'

A94-1F:
(SEQ ID NO: 51)
5'-gtctatttaactcagtattcagaaacaacaaaagttcttctctac
ataaaattttcctattttagtgatcagtgaaggaaatcaagaaaata
aatg-3'

A94-1RC:
(SEQ ID NO: 52)
5'-catttattttcttgatttccttcactgatcactaaaataggaaa
attttatgtagagaagaacttttgttgtttctgaatactgagttaaat
agac-3'

Xa-1F:
(SEQ ID NO: 53)
5'-actctagagtctatttaactcagtattcag-3'

(2) Preparation and Selection of Recombinant *Arabidopsis*, and Expression Level Analysis.

Figure 8:
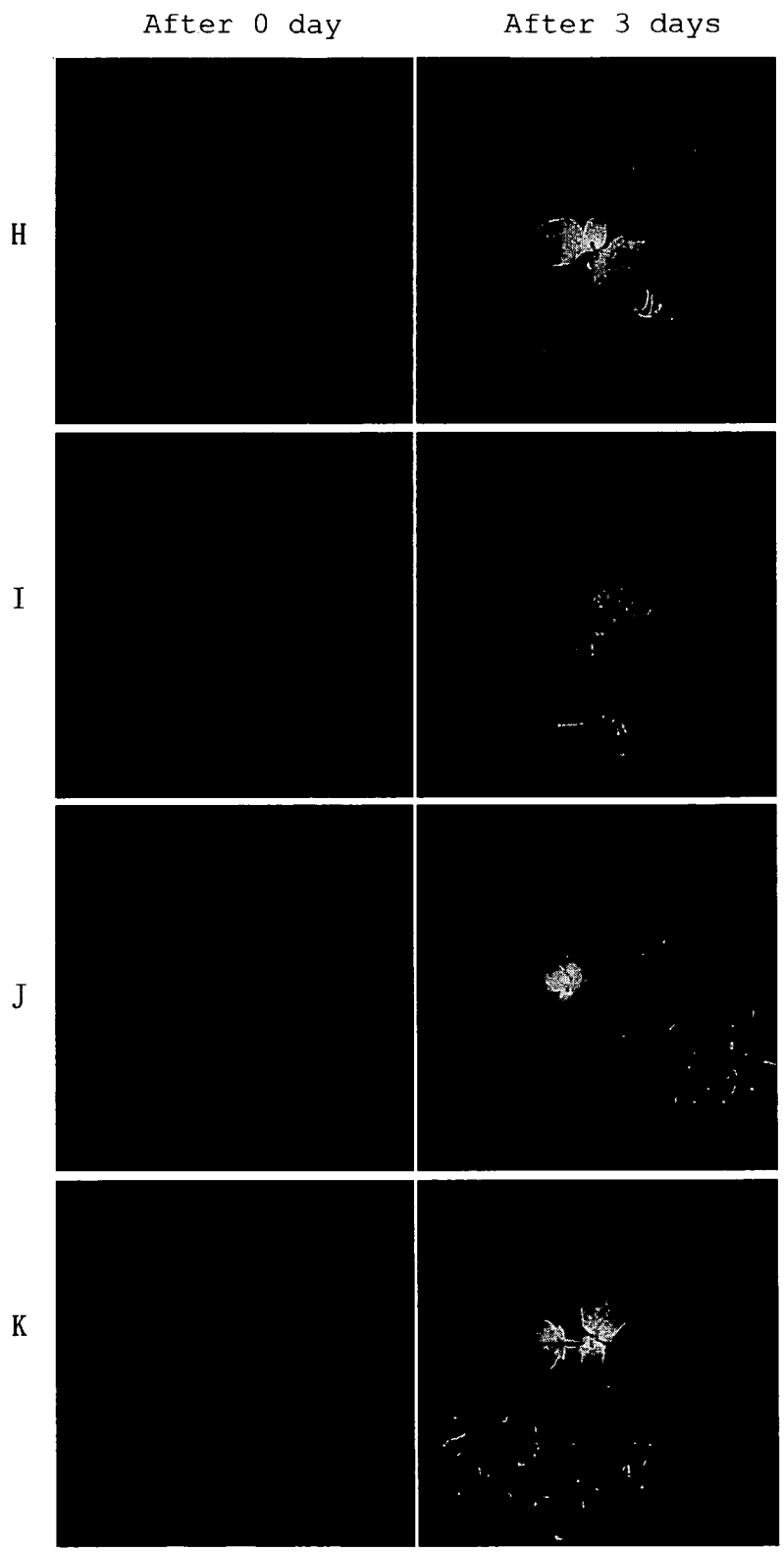
FIG. 8 is a view showing emission states of fluorescence of GFP in a recombinant *Arabidopsis* to which a copper ion-inducible sGFP gene expression vector has been introduced. In each case, the left hand shows the state on 0 day after the induced expression treatment and the right hand shows the state on 3 days after the induced expression treatment.

Each of vectors H to K prepared was introduced into *Agrobacterium* (*Agrobacterium tumefaciens* strain C58C1). The obtained *Agrobacterium* was cultured in an LB agar medium (0.5% yeast extract, 1.0% Bactotriptone, 0.5% sodium chloride, 1% agar) containing 50 mg/L of kanamycin, 100 mg/L of ampicillin and 100 mg/L of rifampicin, and a drug-resistant colony was selected to obtain recombinant *Agrobacterium*. *Arabidopsis* (*Arabidopsis thaliana* ecotype Columbia) was infected by the obtained recombinant *Agrobacterium* according to the method described in Model Plant Laboratory Manual (edited by Iwabuchi Masaki et al, 2000, Springer-Verlag Tokyo Co., Ltd., ISBN 4-431-70881-2 C3045) to introduce genes. After $T_1$ seeds collected from the *Arabidopsis* subjected to gene introduction, seeds were sowed and grown on a modified MS agar medium (MS inorganic salts, B5 vitamin, 1% sucrose, 0.8% agar) containing 20 mg/L of Benlate, 200 mg/L of Claforan, 25 mg/L kanamycin for 11 days, a plant individual resistant to kanamycin was selected. The selected plant individual was transplanted onto a modified MS agar medium (MS inorganic salts, B5 vitamin, 1% sucrose, 0.8% agar) containing 20 mg/L of Benlate, 200 mg/L of Claforan, 25 mg/L kanamycin and grown for additional 6 days. The plant individual of 17 days after sowing was transplanted onto a modified MS agar medium (MS inorganic salts, B5 vitamin, 2% sucrose, 0.8% agar) containing 100 $CuSO_4$ to carry out an induced expression treatment of a target foreign gene (hereinafter, sometimes, referred to as the induced expression treatment). Within one hour after the induced expression treatment (0 day), the fluorescence emission state of GFP of a plant individual was observed by a macro fluorescence microscope VB-G05 (KEYENCE) and fluorescence printed images were obtained by a highly sensitive cooling CCD camera VB-7010 (KEYENCE). As a result, in recombinant *Arabidopsis* in which vectors H to K were introduced, while no fluorescence was observed on 0 day after the induced expression treatment, strong GFP fluorescence was observed 3 days after the inducible expression treatment (see FIG. 8). The culture conditions of growing plant individuals were such that the light period was 23 hours, the dark period was 1 hour and a temperature was 23 to 25° C. up to 11 days after sowing, and thereafter, the light period was 12 hours, the dark period was 12 hours and a temperature was 23 to 25° C.

INDUSTRIAL APPLICABILITY

According to the present invention, in a copper ion inducible system, it is possible to provide a method capable of improving an induction ratio of induced expression of a target foreign gene on a plant.

Sequence Listing Free Text

SEQ ID NO: 1
  Designed oligonucleotide primer for PCR
SEQ ID NO: 2
  Designed oligonucleotide primer for PCR
SEQ ID NO: 3
  Designed oligonucleotide primer for PCR
SEQ ID NO: 4
  Designed oligonucleotide primer for PCR
SEQ ID NO: 5
  Designed oligonucleotide primer for PCR
SEQ ID NO: 6
  Designed oligonucleotide primer for PCR
SEQ ID NO: 7
  Designed oligonucleotide primer for PCR
SEQ ID NO: 8
  Designed oligonucleotide primer for PCR
SEQ ID NO: 9
  Designed oligonucleotide primer for PCR
SEQ ID NO: 10
  Designed oligonucleotide primer for adapter
SEQ ID NO: 11
  Designed oligonucleotide primer for adapter
SEQ ID NO: 12
  Designed oligonucleotide for DNA fragment to be substituted
SEQ ID NO: 13
  Designed oligonucleotide for DNA fragment to be substituted SEQ ID NO: 14
  Designed oligonucleotide primer for PCR
SEQ ID NO: 15
  Designed oligonucleotide primer for PCR
SEQ ID NO: 16
  Designed oligonucleotide primer for PCR
SEQ ID NO: 17
  Designed oligonucleotide primer for PCR
SEQ ID NO: 18
  Designed oligonucleotide primer for PCR
SEQ ID NO: 19
  Designed oligonucleotide primer for PCR
SEQ ID NO: 20
  Designed oligonucleotide primer for PCR
SEQ ID NO: 21
  Designed oligonucleotide primer for PCR
SEQ ID NO: 22
  Designed oligonucleotide for DNA fragment to be inserted
SEQ ID NO: 23
  Designed oligonucleotide for DNA fragment to be inserted
SEQ ID NO: 24
  Designed oligonucleotide for DNA fragment to be substituted
SEQ ID NO: 25
  Designed oligonucleotide for DNA fragment to be substituted
SEQ ID NO: 26
  Designed oligonucleotide primer for PCR
SEQ ID NO: 27
  Designed oligonucleotide primer for PCR
SEQ ID NO: 28
  Designed oligonucleotide for TaqMan probe
SEQ ID NO: 29
  Designed oligonucleotide primer for PCR
SEQ ID NO: 30
  Designed oligonucleotide primer for PCR
SEQ ID NO: 31
  Designed oligonucleotide for TaqMan probe
SEQ ID NO: 32
  Designed oligonucleotide primer for PCR
SEQ ID NO: 33
  Designed oligonucleotide primer for PCR
SEQ ID NO: 34
  Designed oligonucleotide for TaqMan probe
SEQ ID NO: 35
  Designed oligonucleotide primer for PCR
SEQ ID NO: 36
  Designed oligonucleotide primer for PCR
SEQ ID NO: 37
  Designed oligonucleotide primer for PCR
SEQ ID NO: 38
  Designed oligonucleotide primer for PCR
SEQ ID NO: 39
  Designed oligonucleotide primer for PCR
SEQ ID NO: 40
  Designed oligonucleotide primer for PCR
SEQ ID NO: 41
  Designed oligonucleotide primer for PCR
SEQ ID NO: 42
  Designed oligonucleotide primer for PCR
SEQ ID NO: 43
  Designed oligonucleotide primer for PCR
SEQ ID NO: 44
  Designed oligonucleotide primer for PCR
SEQ ID NO: 45
  Designed oligonucleotide primer for PCR
SEQ ID NO: 46
  Designed oligonucleotide primer for PCR
SEQ ID NO: 47
  Designed oligonucleotide primer for PCR
SEQ ID NO: 48
  Designed oligonucleotide primer for PCR
SEQ ID NO: 49
  Designed oligonucleotide primer for PCR
SEQ ID NO: 50
  Designed oligonucleotide primer for PCR
SEQ ID NO: 51
  Designed oligonucleotide for PCR
SEQ ID NO: 52
  Designed oligonucleotide for PCR
SEQ ID NO: 53
  Designed oligonucleotide primer for PCR

The invention claimed is:

1. A method of expression of a target foreign gene in a plant induced by a chemical substance, which comprises:

activating with copper ions a transcription factor encoded by a foreign gene different from the target foreign gene to induce activation of transcription of the target foreign gene by a region having a promoter function contained in the target foreign gene, wherein a nucleotide sequence encoding a yeast ACE1 transcription factor is contained in a gene construct which is constructed so as to comprise a nucleotide sequence of a 5'-untranslated region of a 130k/180k gene of tomato mosaic virus that is amplified by PCR using SEQ ID NO: 20 and SEQ ID NO: 21, wherein the gene construct additionally comprises a nucleotide sequence encoding a transcriptional activation region of a VP16 transcription factor of Herpes simplex virus located downstream from the nucleotide sequence encoding said transcription factor, wherein the transcriptional activation region is that of a transcription factor different from said transcription factor, and wherein said gene construct is constructed so as to additionally comprise an arbitrary promoter upstream from the nucleotide sequence encoding said transcription factor.

2. A gene construct for expression of a target foreign gene in a plant induced by copper ions, with said construct comprising:

(a) a target foreign gene comprising a region having a promoter function and a structural gene region encoding a target foreign protein;
(b) a nucleotide sequence encoding a yeast ACE1 transcription factor encoded by a foreign gene different from said target foreign gene, wherein said transcription factor can be activated by copper ions and activates the region having a promoter function of (a); and
(c) a nucleotide sequence comprising a 5'-untranslated region of a 130k/180k gene of tomato mosaic virus that is amplified by PCR using SEQ ID NO: 20 and SEQ ID NO: 21; and
(d) a nucleotide sequence encoding a transcriptional activation region of a VP16 transcription factor of Herpes simplex virus located downstream from the nucleotide sequence encoding said transcription factor, wherein the transcriptional activation region is that of a transcription factor different from said transcription factor, and
wherein the gene construct additionally comprises an arbitrary promoter upstream from the nucleotide sequence encoding said transcription factor.

3. A transformed plant, wherein the gene construct according to claim 2 is introduced.

4. A method for obtaining a foreign protein, which comprises recovering a target foreign protein from the transformed plant according to claim 3.

* * * * *

SEQUENCE LISTING

```
<160> NUMBER OF SEQ ID NOS: 53

<210> SEQ ID NO 1
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 1
atggatccat ggtcgtaatt aacggg                                          26

<210> SEQ ID NO 2
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 2
tggagctctt attgtgaatg tgagttatg                                       29
```

<210> SEQ ID NO 3
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 3
aactcgagtt gtgaatgtga gttatgcg                                      28

<210> SEQ ID NO 4
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 4
acggctccac cgaccgacgt c                                             21

<210> SEQ ID NO 5
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 5
ctacccaccg tactcgtcaa ttc                                           23

<210> SEQ ID NO 6
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 6
ggacgaactc cacttagacg g                                             21

<210> SEQ ID NO 7
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 7
ccgtctaagt ggagttcgtc c                                             21

<210> SEQ ID NO 8
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 8
tactcgagtc aacggctcca ccgaccgacg t                                  31

<210> SEQ ID NO 9
<211> LENGTH: 35
<212> TYPE: DNA
<213> ORGANISM: Artificial Sequence
<220> FEATURE:
<223> OTHER INFORMATION: Designed oligonucleotide primer for PCR -continued

```
<400> SEQUENCE: 9
aagagctctt acccaccgta ctcgtcaatt ccaag                                35

<210> SEQ ID NO 10
<211> LENGTH: 15
<212> TYPE: DNA
<213> ORGANISM: Artificial Sequence
<220> FEATURE:
<223> OTHER INFORMATION: Designed oligonucleotide for adapter

<400> SEQUENCE: 10
ggccgcgagc tcagt                                                      15

<210> SEQ ID NO 11
<211> LENGTH: 12
<212> TYPE: DNA
<213> ORGANISM: Artificial Sequence
<220> FEATURE:
<223> OTHER INFORMATION: Designed oligonucleotide for adapter

<400> SEQUENCE: 11
gactgagctc gc                                                         12

<210> SEQ ID NO 12
<211> LENGTH: 52
<212> TYPE: DNA
<213> ORGANISM: Artificial Sequence
<220> FEATURE:
<223> OTHER INFORMATION: Designed oligonucleotide for DNA fragment to be
      substituted

<400> SEQUENCE: 12
agcttagcga tgcgtctttt ccgctgaacc gttccagcaa aaaagactag at              52

<210> SEQ ID NO 13
<211> LENGTH: 48
<212> TYPE: DNA
<213> ORGANISM: Artificial Sequence
<220> FEATURE:
<223> OTHER INFORMATION: Designed oligonucleotide for DNA fragment to be
      substituted

<400> SEQUENCE: 13
atctagtctt ttttgctgga acggttcagc ggaaaagacg catcgcta                   48

<210> SEQ ID NO 14
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 14
tagatatcgc aagacccttc ctctatataa gg                                   32

<210> SEQ ID NO 15
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 15
atcctctaga gtcccccgtg ttc                                             23

<210> SEQ ID NO 16
```

<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 16
gctatgacca tgattacgcc aagcttg                                         27

<210> SEQ ID NO 17
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 17
cattgttata tctccttgga tccgtcg                                         27

<210> SEQ ID NO 18
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 18
tagatatctc cacgtccata agggac                                          26

<210> SEQ ID NO 19
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 19
aatctagact gcaggtcgtc ctctcca                                         27

<210> SEQ ID NO 20
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 20
tgtctagagt atttttacaa caattaccaa caac                                 34

<210> SEQ ID NO 21
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 21
aaggatcctg tagttgtaga atgtaaaatg taatg                                35

<210> SEQ ID NO 22
<211> LENGTH: 16
<212> TYPE: DNA
<213> ORGANISM: Artificial Sequence
<220> FEATURE:
<223> OTHER INFORMATION: Designed oligonucleotide for DNA fragment to be
      inserted

<400> SEQUENCE: 22

```
ggtacctcga gtcgac                                                 16
```

<210> SEQ ID NO 23
<211> LENGTH: 16
<212> TYPE: DNA
<213> ORGANISM: Artificial Sequence
<220> FEATURE:
<223> OTHER INFORMATION: Designed oligonucleotide for DNA fragment to be inserted

<400> SEQUENCE: 23

```
gtcgactcga ggtacc                                                 16
```

<210> SEQ ID NO 24
<211> LENGTH: 35
<212> TYPE: DNA
<213> ORGANISM: Artificial Sequence
<220> FEATURE:
<223> OTHER INFORMATION: Designed oligonucleotide for DNA fragment to be substituted

<400> SEQUENCE: 24

```
agcttgaatt cgtcgacggt acctaggacg agctc                            35
```

<210> SEQ ID NO 25
<211> LENGTH: 35
<212> TYPE: DNA
<213> ORGANISM: Artificial Sequence
<220> FEATURE:
<223> OTHER INFORMATION: Designed oligonucleotide for DNA fragment to be substituted

<400> SEQUENCE: 25

```
aattgagctc gtcctaggta ccgtcgacga attca                            35
```

<210> SEQ ID NO 26
<211> LENGTH: 18
<212> TYPE: DNA
<213> ORGANISM: Artificial Sequence
<220> FEATURE:
<223> OTHER INFORMATION: Designed oligonucleotide primer for PCR

<400> SEQUENCE: 26

```
tccgccctga gcaaagac                                               18
```

<210> SEQ ID NO 27
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 27

```
gaactccagc aggaccatgt g                                           21
```

<210> SEQ ID NO 28
<211> LENGTH: 16
<212> TYPE: DNA
<213> ORGANISM: Artificial Sequence
<220> FEATURE:
<223> OTHER INFORMATION: Designed oligonucleotide for taqMan probe

<400> SEQUENCE: 28

```
ccaacgagaa gcgcga                                                 16
```

<210> SEQ ID NO 29

```
<210> SEQ ID NO 29
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 29
cggtggttcc attcttgctt                                              20

<210> SEQ ID NO 30
<211> LENGTH: 19
<212> TYPE: DNA
<213> ORGANISM: Artificial Sequence
<220> FEATURE:
<223> OTHER INFORMATION: Designed oligonucleotide primer for PCR

<400> SEQUENCE: 30
cggccttgga gatccacat                                               19

<210> SEQ ID NO 31
<211> LENGTH: 14
<212> TYPE: DNA
<213> ORGANISM: Artificial Sequence
<220> FEATURE:
<223> OTHER INFORMATION: Designed oligonucleotide for TaqMan probe

<400> SEQUENCE: 31
cctcagcaca ttcc                                                    14

<210> SEQ ID NO 32
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 32
gaagcagctc gaggatggaa                                              20

<210> SEQ ID NO 33
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 33
gacgggttga ctctttctgg at                                           22

<210> SEQ ID NO 34
<211> LENGTH: 17
<212> TYPE: DNA
<213> ORGANISM: Artificial Sequence
<220> FEATURE:
<223> OTHER INFORMATION: Designed oligonucleotide for TaqMan probe

<400> SEQUENCE: 34
accttggctg actacaa                                                 17

<210> SEQ ID NO 35
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 35
```

```
taatctagaa tgtctataaa tataagagac cctc                                    34

<210> SEQ ID NO 36
<211> LENGTH: 28
<212> TYPE: DNA
<213> ORGANISM: Artificial Sequence
<220> FEATURE:
<223> OTHER INFORMATION: Designed oligonucleotide for TaqMan probe

<400> SEQUENCE: 36
atagagctcc taaagtcttc ttcctccg                                           28

<210> SEQ ID NO 37
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 37
taaggatcca tgtctataaa tataagagac cctc                                    34

<210> SEQ ID NO 38
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 38
gaacatctgg atcgaccata accaaagta                                          29

<210> SEQ ID NO 39
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 39
tactttggtt atggtcgatc cagatgttc                                          29

<210> SEQ ID NO 40
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 40
gacacgatga atacctgcag tggga                                              25

<210> SEQ ID NO 41
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 41
tcccactgca ggtattcatc gtgtc                                              25

<210> SEQ ID NO 42
<211> LENGTH: 25
<212> TYPE: DNA
<213> ORGANISM: Artificial Sequence
<220> FEATURE:
```

<223> OTHER INFORMATION: Designed oligonucleotide primer for PCR

<400> SEQUENCE: 42
ctagatatcg caagaccctt cctct                                  25

<210> SEQ ID NO 43
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 43
gtaaaaatac cctctccaaa tgaaatgaac ttc                         33

<210> SEQ ID NO 44
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 44 ggtatttta caacaattac caacaacaac                              30

<210> SEQ ID NO 45
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 45
cattgtaatt gtaaatagta attgtaatgt                             30

<210> SEQ ID NO 46
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 46
acaattacaa tggtgagcaa gggcga                                 26

<210> SEQ ID NO 47
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 47
ttagagctct tacttgtaca gctcgtcc                               28

<210> SEQ ID NO 48
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 48
gactctagag tatttttaca acaattacca ac                          32

<210> SEQ ID NO 49

```
<211> LENGTH: 34
<212> TYPE: DNA
<213> ORGANISM: Artificial Sequence
<220> FEATURE:
<223> OTHER INFORMATION: Designed oligonucleotide primer for PCR

<400> SEQUENCE: 49
gttaaataga ccctctccaa atgaaatgaa cttc                              34

<210> SEQ ID NO 50
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 50
gaaaaataaa tggtgagcaa gggcgag                                     27

<210> SEQ ID NO 51
<211> LENGTH: 97
<212> TYPE: DNA
<213> ORGANISM: Artificial Sequence
<220> FEATURE:
<223> OTHER INFORMATION: Designed oligonucleotide for PCR

<400> SEQUENCE: 51
gtctatttaa ctcagtattc agaaacaaca aaagttcttc tctacataaa attttcctat    60
tttagtgatc agtgaaggaa atcaagaaaa ataaatg                            97

<210> SEQ ID NO 52
<211> LENGTH: 97
<212> TYPE: DNA
<213> ORGANISM: Artificial Sequence
<220> FEATURE:
<223> OTHER INFORMATION: Designed oligonucleotide for PCR

<400> SEQUENCE: 52
catttatttt tcttgatttc cttcactgat cactaaaata ggaaaatttt atgtagagaa    60
gaacttttgt tgtttctgaa tactgagtta aatagac                            97

<210> SEQ ID NO 53
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 53
actctagagt ctatttaact cagtattcag                                  30
```